(12) United States Patent
Veldman et al.

(10) Patent No.: US 12,336,889 B2
(45) Date of Patent: Jun. 24, 2025

(54) ELASTIC COMPOSITE STRUCTURE FOR AN ABSORBENT SANITARY PRODUCT AND AN APPARATUS AND METHOD FOR MAKING SAID ELASTIC COMPOSITE STRUCTURE

(71) Applicant: Curt G. Joa, Inc., Sheboygan Falls, WI (US)

(72) Inventors: Cory D. Veldman, Plymouth, WI (US); David E. Schuette, Kiel, WI (US); Jeffrey W. Fritz, Plymouth, WI (US); Brenton A. Rabe, Howards Grove, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 181 days.

(21) Appl. No.: 17/904,475

(22) PCT Filed: Feb. 16, 2021

(86) PCT No.: PCT/US2021/070155
§ 371 (c)(1),
(2) Date: Aug. 17, 2022

(87) PCT Pub. No.: WO2021/168473
PCT Pub. Date: Aug. 26, 2021

(65) Prior Publication Data
US 2023/0101562 A1    Mar. 30, 2023

Related U.S. Application Data

(60) Provisional application No. 62/977,438, filed on Feb. 17, 2020, provisional application No. 62/977,453, filed on Feb. 17, 2020.

(51) Int. Cl.
*B29C 65/00* (2006.01)
*A61F 13/15* (2006.01)
(Continued)

(52) U.S. Cl.
CPC .. *A61F 13/15593* (2013.01); *A61F 13/15699* (2013.01); *A61F 13/494* (2013.01);
(Continued)

(58) Field of Classification Search
CPC ..... B29C 65/08; B29C 65/083; B29C 65/086; B29C 66/344; B29C 66/4332
See application file for complete search history.

(56) References Cited

U.S. PATENT DOCUMENTS

| 3,580,783 A | 5/1971 | Glaze |
| 3,589,100 A | 6/1971 | Konars et al. |

(Continued)

FOREIGN PATENT DOCUMENTS

| CN | 101868210 B | 9/2014 |
| EP | 0274752 A2 | 7/1988 |

(Continued)

OTHER PUBLICATIONS

Japanese Office Action for Application No. JP2020-541440 Dated Feb. 7, 2023.
(Continued)

*Primary Examiner* — Philip C Tucker
*Assistant Examiner* — Nickolas R Harm
(74) *Attorney, Agent, or Firm* — Klintworth & Rozenblat LLP

(57) ABSTRACT

A machine and method for manufacturing an elastic composite structure for disposable sanitary products involves manufacturing the elastic composite structure with an elasticized leg and leg cuff region in a manner that minimizes or eliminates the use of consumable adhesives. The elastic composite structure includes pairs of leg bonds and cuff bonds that are formed without adhesive and anchor respective leg and cuff elastic threads in position relative to facing (Continued)

web layers. The leg bonds and cuff bonds are formed using one or more anvils that include discrete raised projections.

7 Claims, 22 Drawing Sheets

(51) Int. Cl.
*A61F 13/494* (2006.01)
*B29C 65/08* (2006.01)

(52) U.S. Cl.
CPC ....... *A61F 2013/4948* (2013.01); *B29C 65/08* (2013.01); *B29C 65/083* (2013.01); *B29C 65/086* (2013.01); *B29C 66/344* (2013.01); *B29C 66/4332* (2013.01)

(56) References Cited

U.S. PATENT DOCUMENTS

| | | | |
|---|---|---|---|
| 3,622,434 A | 11/1971 | Newman | |
| 3,658,064 A | 4/1972 | Pociluyko | |
| 3,668,054 A | 6/1972 | Stumpf | |
| 3,844,869 A | 10/1974 | Rust, Jr. | |
| 3,884,227 A | 5/1975 | Lutz et al. | |
| 3,982,988 A | 9/1976 | Heimberger | |
| 3,993,532 A | 11/1976 | McDonald et al. | |
| 4,088,731 A | 5/1978 | Groome | |
| 4,305,988 A | 12/1981 | Koecher | |
| 4,305,998 A | 12/1981 | Manty et al. | |
| 4,333,978 A | 6/1982 | Koecher | |
| 4,336,203 A | 6/1982 | Zucker et al. | |
| 4,443,291 A | 4/1984 | Reed | |
| 4,485,819 A | 12/1984 | Igl | |
| 4,662,005 A | 5/1987 | Grier-Idris | |
| 4,770,656 A | 9/1988 | Proxmire et al. | |
| 4,808,176 A | 2/1989 | Kielpikowski | |
| 4,833,734 A | 5/1989 | Der Estephanian | |
| 4,834,738 A | 5/1989 | Kielpikowski et al. | |
| 4,834,741 A | 5/1989 | Sabee | |
| 4,842,596 A | 6/1989 | Kielpikowski et al. | |
| 4,863,542 A | 9/1989 | Oshefsky et al. | |
| 4,919,738 A | 4/1990 | Ball et al. | |
| 4,977,011 A | 12/1990 | Smith | |
| 5,094,717 A | 3/1992 | Manning et al. | |
| 5,163,932 A | 11/1992 | Nomura et al. | |
| 5,167,897 A * | 12/1992 | Weber ............... | A61F 13/15593 264/290.2 |
| 5,353,798 A | 10/1994 | Sieben | |
| 5,468,320 A | 11/1995 | Zafiroglu | |
| 5,530,979 A | 7/1996 | Whitley | |
| 5,561,863 A | 10/1996 | Carlson, II | |
| 5,618,378 A | 4/1997 | Cahill | |
| 5,624,420 A | 4/1997 | Bridges et al. | |
| 5,643,395 A | 7/1997 | Hinton | |
| 5,643,396 A | 7/1997 | Rajala et al. | |
| 5,660,657 A | 8/1997 | Rajala et al. | |
| 5,694,925 A | 12/1997 | Reese et al. | |
| 5,699,791 A | 12/1997 | Sukiennik et al. | |
| 5,707,470 A | 1/1998 | Rajala et al. | |
| 5,711,847 A | 1/1998 | Rajala et al. | |
| 5,745,922 A | 5/1998 | Rajala et al. | |
| 5,769,993 A | 6/1998 | Baldauf | |
| 5,789,065 A | 8/1998 | Haffner et al. | |
| 5,797,895 A | 8/1998 | Widlund et al. | |
| 5,803,075 A | 9/1998 | Yavitz | |
| 5,813,398 A | 9/1998 | Baird et al. | |
| 5,817,584 A | 10/1998 | Singer et al. | |
| 5,883,026 A | 3/1999 | Reader et al. | |
| 5,934,275 A | 8/1999 | Gazzara | |
| 5,954,055 A | 9/1999 | Miyake | |
| D424,688 S | 5/2000 | Bryant et al. | |
| 6,055,982 A | 5/2000 | Brunson et al. | |
| 6,057,024 A | 5/2000 | Mleziva et al. | |
| 6,062,220 A | 5/2000 | Whitaker et al. | |
| 6,123,077 A | 9/2000 | Bostock et al. | |
| 6,125,849 A | 10/2000 | Williams et al. | |
| 6,165,298 A | 12/2000 | Samida et al. | |
| 6,173,712 B1 | 1/2001 | Brunson | |
| 6,197,404 B1 | 3/2001 | Varona | |
| 6,213,125 B1 | 4/2001 | Reese et al. | |
| 6,217,889 B1 | 4/2001 | Lorenzi et al. | |
| 6,235,137 B1 | 5/2001 | Van Eperen et al. | |
| 6,257,235 B1 | 7/2001 | Bowen | |
| 6,279,570 B1 | 8/2001 | Mittelstadt et al. | |
| 6,291,039 B1 | 9/2001 | Combe et al. | |
| 6,295,714 B1 | 10/2001 | Roychowdhury et al. | |
| 6,332,465 B1 | 12/2001 | Xue et al. | |
| 6,340,782 B1 | 1/2002 | Kling et al. | |
| 6,354,296 B1 | 3/2002 | Baumann et al. | |
| 6,394,090 B1 | 5/2002 | Chen et al. | |
| 6,427,693 B1 | 8/2002 | Blackstock et al. | |
| 6,460,539 B1 | 10/2002 | Japuntich et al. | |
| 6,482,278 B1 | 11/2002 | McCabe et al. | |
| 6,484,722 B2 | 11/2002 | Bostock et al. | |
| 6,506,474 B2 | 1/2003 | Tsuji | |
| 6,534,694 B2 | 3/2003 | Kling et al. | |
| 6,536,434 B1 | 3/2003 | Bostock et al. | |
| 6,541,679 B2 | 4/2003 | Betrabet et al. | |
| 6,568,392 B1 | 5/2003 | Bostock et al. | |
| 6,584,976 B2 | 7/2003 | Japuntich et al. | |
| 6,604,524 B1 | 8/2003 | Curran et al. | |
| 6,613,955 B1 | 9/2003 | Lindsay et al. | |
| 6,623,837 B2 | 9/2003 | Morman et al. | |
| 6,644,314 B1 | 11/2003 | Elsberg | |
| 6,652,693 B2 | 11/2003 | Burriss et al. | |
| 6,673,980 B1 | 1/2004 | Varona et al. | |
| 6,676,062 B1 | 1/2004 | Herhaus | |
| 6,701,992 B1 | 3/2004 | Pasquale et al. | |
| 6,712,922 B2 | 3/2004 | Sorenson et al. | |
| 6,715,489 B2 | 4/2004 | Bostock et al. | |
| 6,722,366 B2 | 4/2004 | Bostock et al. | |
| 6,730,188 B2 | 5/2004 | Sanders | |
| 6,761,710 B2 | 7/2004 | Acchioli et al. | |
| 6,780,263 B2 | 8/2004 | Delisle | |
| 6,843,872 B2 | 1/2005 | Morman | |
| 6,886,563 B2 | 5/2005 | Bostock et al. | |
| 6,889,622 B2 | 5/2005 | Marcangelo | |
| 6,914,018 B1 | 7/2005 | Uitenbroek et al. | |
| 6,928,657 B2 | 8/2005 | Bell et al. | |
| 6,953,452 B2 | 10/2005 | Popp et al. | |
| 7,008,496 B2 | 3/2006 | Morman | |
| 7,021,227 B2 | 4/2006 | Marcangelo | |
| 7,025,841 B2 | 4/2006 | Owen | |
| 7,044,131 B2 | 5/2006 | Griesbach et al. | |
| 7,069,930 B2 | 7/2006 | Bostock et al. | |
| 7,118,558 B2 | 10/2006 | Wu et al. | |
| 7,198,688 B2 | 4/2007 | Mortell et al. | |
| 7,211,531 B2 | 5/2007 | Schneider et al. | |
| 7,217,261 B2 | 5/2007 | Otsubo et al. | |
| 7,290,545 B2 | 11/2007 | Kleman et al. | |
| 7,316,840 B2 | 1/2008 | Neculescu et al. | |
| 7,361,241 B2 | 4/2008 | Barth et al. | |
| 7,378,566 B2 | 5/2008 | Soerens et al. | |
| 7,464,516 B2 | 12/2008 | Johnson | |
| 7,469,427 B2 | 12/2008 | Yang et al. | |
| 7,507,680 B2 | 3/2009 | Middlesworth et al. | |
| 7,582,348 B2 | 9/2009 | Ando et al. | |
| 7,617,787 B2 | 11/2009 | Marcangelo | |
| 7,619,167 B2 | 11/2009 | Lee et al. | |
| 7,638,014 B2 | 12/2009 | Coose et al. | |
| 7,642,398 B2 | 1/2010 | Jarpenberg et al. | |
| 7,691,138 B2 | 4/2010 | Stenzel et al. | |
| 7,708,849 B2 | 5/2010 | McCabe | |
| 7,722,734 B2 | 5/2010 | Otsubo | |
| 7,725,948 B2 | 6/2010 | Steindorf | |
| 7,799,967 B2 | 9/2010 | Ranganathan et al. | |
| 7,833,369 B2 | 11/2010 | Zhou et al. | |
| 7,845,351 B2 | 12/2010 | Mathis et al. | |
| 7,861,756 B2 | 1/2011 | Jenquin et al. | |
| 7,901,392 B2 | 3/2011 | Kline et al. | |
| 7,955,418 B2 | 6/2011 | Claussen et al. | |
| 7,981,231 B2 | 7/2011 | Schneider et al. | |
| 8,007,484 B2 | 8/2011 | McCabe et al. | |
| 8,074,660 B2 | 12/2011 | Duffy | |

(56) References Cited

U.S. PATENT DOCUMENTS

| | | |
|---|---|---|
| 8,075,543 B2 | 12/2011 | Okuda |
| 8,091,550 B2 | 1/2012 | Steindorf |
| 8,109,916 B2 | 2/2012 | Wennerbaeck |
| 8,142,411 B2 | 3/2012 | Kline et al. |
| 8,146,594 B2 | 4/2012 | Bostock et al. |
| 8,182,457 B2 | 5/2012 | Olson et al. |
| 8,182,624 B2 | 5/2012 | Handziak |
| 8,207,395 B2 | 6/2012 | Soerens et al. |
| 8,268,444 B2 | 9/2012 | Okaya |
| 8,282,617 B2 | 10/2012 | Kaneda |
| 8,298,205 B2 | 10/2012 | Norrby et al. |
| 8,308,706 B2 | 11/2012 | Fukae |
| 8,323,257 B2 | 12/2012 | Melik et al. |
| 8,328,820 B2 | 12/2012 | Diamant et al. |
| 8,360,067 B2 | 1/2013 | Duffy |
| 8,375,950 B2 | 2/2013 | Bostock et al. |
| 8,435,223 B2 | 5/2013 | Roe et al. |
| 8,440,043 B1 | 5/2013 | Schneider et al. |
| 8,470,946 B1 | 6/2013 | Carlson |
| 8,528,560 B2 | 9/2013 | Duffy |
| 8,562,777 B2 | 10/2013 | Drake |
| 8,585,667 B2 | 11/2013 | Roe et al. |
| 8,622,059 B2 | 1/2014 | Kleman |
| 8,640,704 B2 | 2/2014 | Spoo et al. |
| 8,647,319 B2 | 2/2014 | Een et al. |
| 8,652,114 B2 | 2/2014 | Roe et al. |
| 8,652,115 B2 | 2/2014 | Roe et al. |
| 8,669,409 B2 | 3/2014 | Roe |
| 8,702,671 B2 | 4/2014 | Tsang et al. |
| 8,740,128 B2 | 6/2014 | Oravits et al. |
| 8,741,083 B2 | 6/2014 | Wennerbaeck et al. |
| 8,758,786 B2 | 6/2014 | Hassler |
| 8,771,449 B2 | 7/2014 | Takino et al. |
| 8,784,395 B2 | 7/2014 | Roe et al. |
| 8,784,397 B2 | 7/2014 | Chang et al. |
| 8,808,263 B2 | 8/2014 | Roe et al. |
| 8,881,729 B2 | 11/2014 | Duffy |
| 8,926,579 B2 | 1/2015 | Wang et al. |
| 8,932,273 B2 | 1/2015 | Roe et al. |
| 8,936,586 B2 | 1/2015 | Roe |
| 8,992,497 B2 | 3/2015 | Roe et al. |
| 8,998,870 B2 | 4/2015 | Roe |
| 9,011,402 B2 | 4/2015 | Roe et al. |
| 9,011,404 B2 | 4/2015 | Kobayashi et al. |
| 9,012,013 B2 | 4/2015 | Duffy |
| 9,028,462 B2 | 5/2015 | Poole et al. |
| 9,056,033 B2 | 6/2015 | Fenske |
| 9,060,905 B2 | 6/2015 | Wang et al. |
| 9,078,789 B2 | 7/2015 | Wang et al. |
| 9,078,792 B2 | 7/2015 | Ruiz |
| 9,089,456 B2 | 7/2015 | Roe et al. |
| 9,095,478 B2 | 8/2015 | Roe |
| 9,180,059 B2 | 11/2015 | Roe et al. |
| 9,301,881 B2 | 4/2016 | Ando et al. |
| 9,387,138 B2 | 7/2016 | Roe |
| 9,539,735 B2 | 1/2017 | Ferguson et al. |
| 9,603,395 B2 | 3/2017 | Duffy |
| 9,603,396 B2 | 3/2017 | Duffy |
| 9,615,612 B2 | 4/2017 | Duffy |
| 9,770,057 B2 | 9/2017 | Duffy |
| 9,770,058 B2 | 9/2017 | Angadjivand et al. |
| 9,770,611 B2 | 9/2017 | Facer et al. |
| 9,809,414 B2 | 11/2017 | Fritz et al. |
| 9,868,002 B2 | 1/2018 | Duffy |
| 9,913,764 B2 | 3/2018 | Thomas et al. |
| 10,040,621 B2 | 8/2018 | Duffy et al. |
| 10,130,833 B2 | 11/2018 | Angadjivand et al. |
| 10,137,321 B2 | 11/2018 | Martin |
| 10,143,246 B2 | 12/2018 | Houde et al. |
| D837,970 S | 1/2019 | Henderson et al. |
| 10,182,603 B2 | 1/2019 | Duffy |
| 10,213,348 B2 | 2/2019 | Gualtieri et al. |
| 10,227,202 B2 | 3/2019 | Pamperin et al. |
| 10,259,165 B2 | 4/2019 | Ehlert et al. |
| D848,678 S | 5/2019 | Andrews |
| 10,314,346 B2 | 6/2019 | Potnis et al. |
| 10,329,110 B2 | 6/2019 | Dotta |
| 10,457,436 B2 | 10/2019 | Spencer et al. |
| 10,492,547 B2 | 12/2019 | Weber et al. |
| 10,494,221 B2 | 12/2019 | Harris et al. |
| 10,518,996 B2 | 12/2019 | Adami |
| 10,537,479 B2 | 1/2020 | Schuette et al. |
| 10,596,045 B2 | 3/2020 | Koshijima et al. |
| 10,596,047 B2 | 3/2020 | Coenen et al. |
| 10,751,228 B2 | 8/2020 | Kurohara et al. |
| 10,758,428 B2 | 9/2020 | Nakamura et al. |
| 10,786,398 B2 | 9/2020 | Koshijima et al. |
| 10,792,194 B2 | 10/2020 | Hohm et al. |
| 10,889,066 B2 | 1/2021 | Begrow et al. |
| 10,893,986 B2 | 1/2021 | Manabe et al. |
| 10,973,703 B2 | 4/2021 | Coenen et al. |
| 11,020,281 B2 | 6/2021 | Ishikawa |
| 11,020,286 B2 | 6/2021 | Kaufman et al. |
| 11,117,771 B2 | 9/2021 | Hada et al. |
| 11,129,753 B2 | 9/2021 | Schneider et al. |
| 11,141,321 B2 | 10/2021 | Schneider et al. |
| 11,147,717 B2 | 10/2021 | Schneider et al. |
| 11,173,072 B2 | 11/2021 | Fritz |
| 11,191,676 B2 | 12/2021 | Koshijima et al. |
| 11,219,555 B2 | 1/2022 | Schneider et al. |
| 11,254,062 B2 | 2/2022 | Ehlert et al. |
| 11,254,066 B2 | 2/2022 | Begrow et al. |
| 11,399,989 B2 | 8/2022 | Polidori et al. |
| 11,433,620 B2 | 9/2022 | Ehlert et al. |
| 11,701,268 B2 | 7/2023 | Andrews et al. |
| 2001/0025683 A1 | 10/2001 | Burriss et al. |
| 2001/0034508 A1 | 10/2001 | Betrabet et al. |
| 2001/0044250 A1 | 11/2001 | Tsuji |
| 2002/0092604 A1 | 7/2002 | McCabe et al. |
| 2002/0116027 A1 | 8/2002 | Egan et al. |
| 2002/0117575 A1 | 8/2002 | Gilmore et al. |
| 2002/0119288 A1 | 8/2002 | Morman et al. |
| 2002/0157778 A1 | 10/2002 | Sorenson et al. |
| 2003/0051803 A1 | 3/2003 | Sanders |
| 2003/0120250 A1 | 6/2003 | Betrabet et al. |
| 2003/0124306 A1 | 7/2003 | Morman |
| 2003/0125706 A1 | 7/2003 | Popp et al. |
| 2003/0125707 A1 | 7/2003 | Popp et al. |
| 2003/0135185 A1 | 7/2003 | Crowther |
| 2003/0144643 A1 | 7/2003 | Jarpenberg et al. |
| 2004/0005832 A1 | 1/2004 | Neculescu et al. |
| 2004/0059280 A1 | 3/2004 | Makower et al. |
| 2004/0112509 A1 | 6/2004 | Morman |
| 2004/0116885 A1 | 6/2004 | Soerens et al. |
| 2004/0127614 A1 | 7/2004 | Jiang et al. |
| 2004/0138635 A1 | 7/2004 | Soerens et al. |
| 2004/0158217 A1 | 8/2004 | Wu et al. |
| 2004/0192140 A1 | 9/2004 | Schneider et al. |
| 2004/0219854 A1 | 11/2004 | Groitzsch et al. |
| 2004/0226645 A1 | 11/2004 | Owen |
| 2004/0243085 A1 | 12/2004 | Veith et al. |
| 2004/0261230 A1 | 12/2004 | Neeb et al. |
| 2005/0095942 A1 | 5/2005 | Mueller et al. |
| 2005/0101216 A1 | 5/2005 | Middlesworth et al. |
| 2005/0131374 A1 | 6/2005 | Otsubo et al. |
| 2005/0142331 A1 | 6/2005 | Anderson et al. |
| 2005/0148261 A1 | 7/2005 | Close et al. |
| 2005/0176029 A1 | 8/2005 | Heller et al. |
| 2005/0183646 A1 | 8/2005 | Marcangelo |
| 2005/0216058 A1 | 9/2005 | Egan et al. |
| 2005/0228350 A1 | 10/2005 | Ranganathan et al. |
| 2006/0009104 A1 | 1/2006 | Schneider et al. |
| 2006/0069373 A1 | 3/2006 | Schlinz et al. |
| 2006/0099871 A1 | 5/2006 | Poruthoor et al. |
| 2006/0130964 A1 | 6/2006 | McCabe |
| 2006/0135923 A1 | 6/2006 | Boggs et al. |
| 2006/0135932 A1 | 6/2006 | Abuto et al. |
| 2006/0138693 A1 | 6/2006 | Tuman et al. |
| 2006/0149208 A1 | 7/2006 | Carr |
| 2006/0180068 A1 | 8/2006 | Marcangelo |
| 2006/0184149 A1 | 8/2006 | Kasai et al. |
| 2006/0224137 A1 | 10/2006 | McCabe et al. |
| 2006/0228969 A1 | 10/2006 | Erdman |
| 2006/0238757 A1 | 10/2006 | Silcott |

(56) References Cited

U.S. PATENT DOCUMENTS

| | | |
|---|---|---|
| 2006/0270302 A1 | 11/2006 | Ando et al. |
| 2007/0000021 A1 | 1/2007 | Yang et al. |
| 2007/0068529 A1 | 3/2007 | Kalatoor et al. |
| 2007/0131335 A1 | 6/2007 | Zhou et al. |
| 2007/0175477 A1 | 8/2007 | Baggett |
| 2007/0218245 A1 | 9/2007 | Schneider et al. |
| 2007/0286987 A1 | 12/2007 | Anderson et al. |
| 2008/0103460 A1 | 5/2008 | Close et al. |
| 2008/0110554 A1 | 5/2008 | Otsubo |
| 2008/0169373 A1 | 7/2008 | Andrews et al. |
| 2008/0262455 A1 | 10/2008 | Soerens et al. |
| 2008/0312625 A1 | 12/2008 | Hundorf et al. |
| 2009/0134049 A1 | 5/2009 | Melik et al. |
| 2009/0163940 A1 | 6/2009 | Sliwa |
| 2009/0208703 A1 | 8/2009 | Wennerbaeck et al. |
| 2009/0242098 A1 | 10/2009 | Handziak |
| 2009/0306616 A1 | 12/2009 | Wennerbaeck |
| 2009/0326503 A1 | 12/2009 | Lakso et al. |
| 2009/0326504 A1 | 12/2009 | Kaneda |
| 2010/0015190 A1 | 1/2010 | Hassler |
| 2010/0076390 A1 | 3/2010 | Norrby et al. |
| 2010/0076394 A1 | 3/2010 | Hayase et al. |
| 2010/0087352 A1 | 4/2010 | Mason |
| 2010/0286709 A1 | 11/2010 | Diamant et al. |
| 2010/0298798 A1 | 11/2010 | Lakso et al. |
| 2010/0324513 A1 | 12/2010 | Wennerbaeck |
| 2011/0055998 A1 | 3/2011 | Tai et al. |
| 2011/0061786 A1 | 3/2011 | Mason |
| 2011/0067797 A1 | 3/2011 | Schneider et al. |
| 2011/0118689 A1 | 5/2011 | Een et al. |
| 2011/0152811 A1 | 6/2011 | Bing-Wo et al. |
| 2011/0184372 A1 | 7/2011 | Esping et al. |
| 2011/0192888 A1 | 8/2011 | Tai et al. |
| 2011/0251576 A1 | 10/2011 | Ando et al. |
| 2011/0257616 A1 | 10/2011 | Lakso et al. |
| 2012/0088103 A1 | 4/2012 | Sugiura et al. |
| 2012/0095429 A1 | 4/2012 | Kobayashi et al. |
| 2012/0123367 A1 | 5/2012 | Melik et al. |
| 2012/0123368 A1 | 5/2012 | Melik et al. |
| 2012/0123369 A1 | 5/2012 | Melik et al. |
| 2012/0123370 A1 | 5/2012 | Melik et al. |
| 2012/0123371 A1 | 5/2012 | Melik et al. |
| 2012/0123372 A1 | 5/2012 | Melik et al. |
| 2012/0123373 A1 | 5/2012 | Melik et al. |
| 2012/0175064 A1 | 7/2012 | Yamamoto |
| 2012/0228988 A1 | 9/2012 | Cutsforth |
| 2012/0321856 A1 | 12/2012 | Afshari |
| 2012/0328841 A1 | 12/2012 | Afshari |
| 2012/0328842 A1 | 12/2012 | Afshari |
| 2013/0011601 A1 | 1/2013 | Fenske |
| 2013/0012899 A1 | 1/2013 | Fenske |
| 2013/0042411 A1 | 2/2013 | Vitale |
| 2013/0048191 A1 | 2/2013 | Durrance et al. |
| 2013/0079797 A1 | 3/2013 | Diamant et al. |
| 2013/0157012 A1 | 6/2013 | Qin et al. |
| 2013/0165896 A1 | 6/2013 | Carbonari |
| 2013/0255865 A1 | 10/2013 | Brown et al. |
| 2014/0093687 A1 | 4/2014 | Humiston et al. |
| 2014/0099469 A1 | 4/2014 | Abuto et al. |
| 2014/0102650 A1 | 4/2014 | Qin et al. |
| 2014/0180126 A1 | 6/2014 | Millett et al. |
| 2015/0050462 A1 | 2/2015 | Schroer, Jr. |
| 2015/0119219 A1* | 4/2015 | Sina .................. A61F 13/15699 493/343 |
| 2015/0164705 A1 | 6/2015 | Thomas et al. |
| 2016/0058624 A1 | 3/2016 | Hohm et al. |
| 2016/0228305 A1 | 8/2016 | Gualtieri et al. |
| 2016/0288407 A1 | 10/2016 | Ehlert et al. |
| 2016/0331600 A1 | 11/2016 | Polidori et al. |
| 2017/0113366 A1 | 4/2017 | Ferguson et al. |
| 2017/0281417 A1 | 10/2017 | Ishikawa |
| 2018/0027899 A1 | 2/2018 | Facer et al. |
| 2018/0042788 A1 | 2/2018 | Kurohara et al. |
| 2018/0093444 A1 | 4/2018 | Begrow et al. |
| 2018/0140473 A1 | 5/2018 | Koshijima et al. |
| 2018/0147095 A1 | 5/2018 | Koshijima et al. |
| 2018/0168880 A1 | 6/2018 | Schneider et al. |
| 2018/0169964 A1 | 6/2018 | Schneider et al. |
| 2018/0170027 A1 | 6/2018 | Schneider et al. |
| 2018/0280209 A1 | 10/2018 | Manabe et al. |
| 2019/0000162 A1 | 1/2019 | Houde |
| 2019/0021916 A1 | 1/2019 | Ishikawa |
| 2019/0070041 A1 | 3/2019 | Schneider et al. |
| 2019/0209396 A1 | 7/2019 | Nakamura et al. |
| 2019/0224053 A1 | 7/2019 | Nakamura et al. |
| 2019/0231606 A1 | 8/2019 | Andrews et al. |
| 2019/0274895 A1 | 9/2019 | Chen et al. |
| 2019/0358093 A1 | 11/2019 | Kaufman et al. |
| 2019/0374398 A1 | 12/2019 | Coenen et al. |
| 2019/0374404 A1 | 12/2019 | Ninomiya et al. |
| 2020/0039152 A1 | 2/2020 | Ehlert et al. |
| 2020/0179180 A1 | 6/2020 | Koshijima et al. |
| 2020/0197230 A1 | 6/2020 | Ohtsubo |
| 2020/0206040 A1 | 7/2020 | Andrews et al. |
| 2020/0206043 A1 | 7/2020 | Coenen et al. |
| 2020/0214901 A1 | 7/2020 | Andrews et al. |
| 2020/0268567 A1 | 8/2020 | Coenen et al. |
| 2020/0297551 A1 | 9/2020 | Andrews et al. |
| 2020/0298545 A1 | 9/2020 | Andrews et al. |
| 2020/0299883 A1 | 9/2020 | Begrow et al. |
| 2020/0360191 A1 | 11/2020 | Nakamura et al. |
| 2020/0361158 A1 | 11/2020 | Sugiura et al. |
| 2021/0000657 A1 | 1/2021 | Hohm et al. |
| 2021/0059866 A1 | 3/2021 | Fritz et al. |
| 2021/0100695 A1 | 4/2021 | Ishibashi et al. |
| 2021/0205152 A1 | 7/2021 | Polidori et al. |
| 2021/0252796 A1 | 8/2021 | Ehlert et al. |
| 2021/0267818 A1 | 9/2021 | Kaufman et al. |
| 2022/0000676 A1 | 1/2022 | Schneider et al. |
| 2022/0071809 A1 | 3/2022 | Fritz |
| 2022/0151840 A1 | 5/2022 | Mueller et al. |
| 2022/0211553 A1 | 7/2022 | Manabe |
| 2022/0218534 A1 | 7/2022 | Minami et al. |
| 2022/0250331 A1 | 8/2022 | Weiler et al. |
| 2022/0324669 A1 | 10/2022 | Follen et al. |
| 2023/0339714 A1 | 10/2023 | Roehrborn et al. |

FOREIGN PATENT DOCUMENTS

| | | | |
|---|---|---|---|
| EP | 0330716 | A2 | 9/1989 |
| EP | 0168225 | B1 | 3/1991 |
| EP | 0307871 | B1 | 12/1992 |
| EP | 0386324 | B1 | 6/1993 |
| EP | 0685586 | A2 | 12/1995 |
| EP | 0886480 | B1 | 12/2001 |
| EP | 1166721 | A2 | 1/2002 |
| EP | 1035808 | B1 | 3/2004 |
| EP | 1024721 | B1 | 9/2004 |
| EP | 1351815 | B1 | 2/2005 |
| EP | 1555000 | A2 | 7/2005 |
| EP | 0677284 | B2 | 8/2005 |
| EP | 1388410 | B1 | 10/2005 |
| EP | 1448824 | B1 | 10/2005 |
| EP | 1236827 | B1 | 1/2006 |
| EP | 1029521 | B1 | 4/2006 |
| EP | 1138471 | B1 | 6/2006 |
| EP | 1159942 | B1 | 7/2006 |
| EP | 1641417 | B1 | 6/2007 |
| EP | 1547558 | B1 | 10/2008 |
| EP | 1290289 | B1 | 12/2008 |
| EP | 1330355 | B1 | 3/2009 |
| EP | 1263989 | B1 | 5/2009 |
| EP | 1330222 | B1 | 8/2009 |
| EP | 1458553 | B1 | 9/2009 |
| EP | 2103427 | A2 | 9/2009 |
| EP | 1610950 | B1 | 10/2009 |
| EP | 1715994 | B1 | 3/2010 |
| EP | 1520569 | B1 | 7/2010 |
| EP | 1586252 | B1 | 8/2010 |
| EP | 1959907 | B1 | 9/2010 |
| EP | 1525345 | B1 | 4/2011 |
| EP | 1882177 | B1 | 6/2011 |
| EP | 1707168 | B1 | 8/2011 |
| EP | 1716831 | B1 | 9/2011 |

(56) References Cited

FOREIGN PATENT DOCUMENTS

| | | | |
|---|---|---|---|
| EP | 2083100 | B1 | 9/2011 |
| EP | 2207926 | B1 | 9/2011 |
| EP | 2219534 | B1 | 9/2011 |
| EP | 2027841 | B1 | 7/2012 |
| EP | 1595017 | B1 | 8/2012 |
| EP | 1891256 | B1 | 8/2012 |
| EP | 2020972 | B1 | 11/2012 |
| EP | 2020974 | B1 | 12/2012 |
| EP | 1685816 | B1 | 1/2013 |
| EP | 2024178 | B1 | 1/2013 |
| EP | 2088980 | B1 | 1/2013 |
| EP | 1272347 | B1 | 4/2013 |
| EP | 1458565 | B1 | 3/2014 |
| EP | 2727521 | A1 | 5/2014 |
| EP | 1575470 | B1 | 6/2014 |
| EP | 2088981 | B1 | 6/2014 |
| EP | 2431013 | B1 | 9/2014 |
| EP | 2441866 | B1 | 2/2015 |
| EP | 2133297 | B1 | 4/2016 |
| EP | 1806117 | B1 | 6/2016 |
| EP | 3028687 | B1 | 3/2017 |
| EP | 1666178 | B1 | 5/2017 |
| EP | 2214614 | B1 | 8/2017 |
| EP | 3092997 | B1 | 8/2017 |
| EP | 2450015 | B1 | 11/2017 |
| EP | 2105115 | B1 | 3/2018 |
| EP | 2116367 | B1 | 4/2018 |
| EP | 2142261 | B1 | 5/2018 |
| EP | 2454957 | B1 | 11/2018 |
| EP | 3117810 | B1 | 7/2019 |
| EP | 3527181 | A1 | 8/2019 |
| EP | 3199132 | B1 | 9/2019 |
| EP | 3056176 | B1 | 10/2019 |
| EP | 3296100 | B1 | 1/2020 |
| EP | 3646830 | A1 | 5/2020 |
| EP | 3677231 | A1 | 7/2020 |
| EP | 3747636 | A1 | 12/2020 |
| EP | 3558192 | B1 | 1/2021 |
| EP | 3558664 | B1 | 4/2021 |
| EP | 3519162 | B1 | 7/2021 |
| EP | 3572052 | B1 | 7/2021 |
| EP | 3558193 | B1 | 8/2021 |
| EP | 3865103 | A1 | 8/2021 |
| EP | 3558191 | B1 | 9/2021 |
| EP | 3275413 | B1 | 10/2021 |
| EP | 3342385 | B1 | 10/2021 |
| EP | 3527182 | B1 | 10/2021 |
| EP | 3675785 | B1 | 11/2021 |
| EP | 3904057 | A1 | 11/2021 |
| EP | 3299167 | B1 | 3/2022 |
| EP | 3960140 | A1 | 3/2022 |
| EP | 3960439 | A1 | 3/2022 |
| EP | 3981371 | A1 | 4/2022 |
| EP | 3675784 | B1 | 10/2022 |
| FR | 2532337 | A1 | 3/1984 |
| JP | H0866424 | A | 3/1996 |
| JP | 2005095574 | A | 4/2005 |
| JP | 2008154998 | A | 7/2008 |
| JP | 2009056156 | A | 3/2009 |
| JP | 2009106667 | A | 5/2009 |
| JP | 5085239 | B2 | 11/2012 |
| JP | 05106990 | B2 | 12/2012 |
| JP | 05124188 | B2 | 1/2013 |
| JP | 2014198179 | A | 10/2014 |
| JP | 2017012459 | A | 1/2017 |
| JP | 2017064130 | A | 4/2017 |
| JP | 06192003 | B2 | 9/2017 |
| JP | 2019030441 | A | 2/2019 |
| KR | 1982464 | B1 | 5/2019 |
| KR | 2013608 | B1 | 8/2019 |
| KR | 2022211 | B1 | 9/2019 |
| RU | 2304047 | C2 | 8/2007 |
| RU | 2010125133 | A | 12/2011 |
| WO | WO1993021788 | A1 | 11/1993 |
| WO | WO0192013 | A1 | 12/2001 |
| WO | WO2009067055 | A1 | 5/2009 |
| WO | WO2011087502 | A1 | 7/2011 |
| WO | WO2014109924 | A1 | 7/2014 |
| WO | WO2014145668 | A1 | 9/2014 |
| WO | WO2016033226 | A1 | 3/2016 |
| WO | WO2016109514 | A1 | 7/2016 |
| WO | WO2016160752 | A1 | 10/2016 |
| WO | WO2016208513 | A1 | 4/2018 |
| WO | WO2018097771 | A1 | 5/2018 |
| WO | 2018118431 | A1 | 6/2018 |
| WO | WO2018118573 | A1 | 6/2018 |
| WO | 2018/154680 | A1 | 8/2018 |
| WO | WO2018160207 | A1 | 9/2018 |
| WO | WO2018160208 | A1 | 9/2018 |
| WO | WO2019070248 | A1 | 4/2019 |
| WO | WO2019125415 | A1 | 6/2019 |
| WO | WO2020198025 | A1 | 10/2020 |
| WO | WO2021043943 | A1 | 3/2021 |

OTHER PUBLICATIONS

Presentation by Thomas Ehlert, VP of RD&E, Aurizon Ultrasonics, LLC, entitled "Adhesive-free, Ultrasonic Elastic Attachment", date at least as early as Nov. 17, 2014, 57 pages.
PCT International Search Report and Written Opinion, Jun. 4, 2021.
PCT International Search Report and Written Opinion, PCT/US2015/047015, dated Nov. 24, 2015, 8 pages.
Notification of Reasons for Refusal issued in Japanese Application No. 2020-147443, dated Oct. 23, 2023, 5 pages.
Notice of refusal issued in connection with Japanese patent application No. JP2022-549304 Dated Sep. 17, 2024, 6 pages.

* cited by examiner

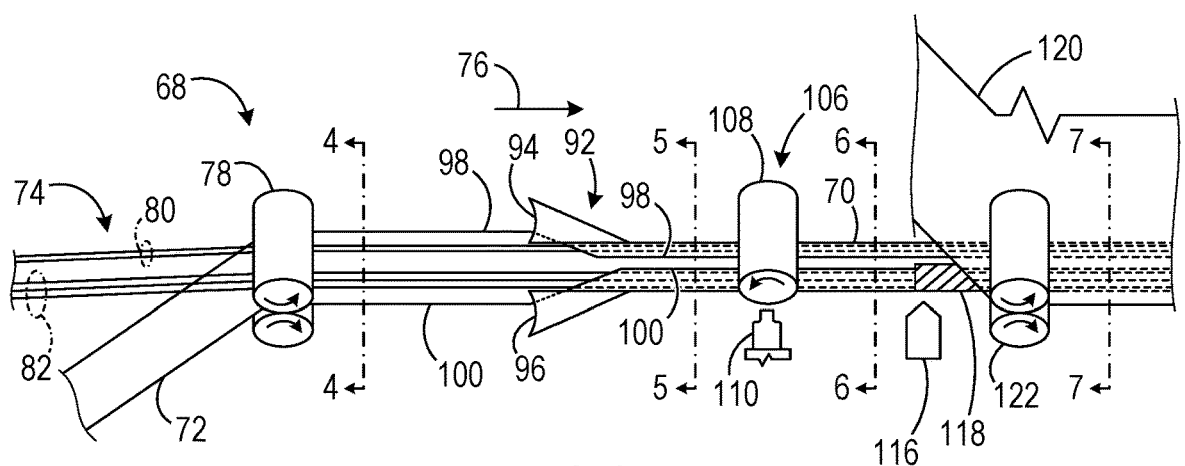

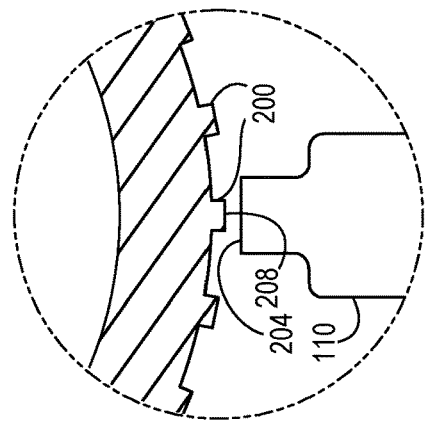
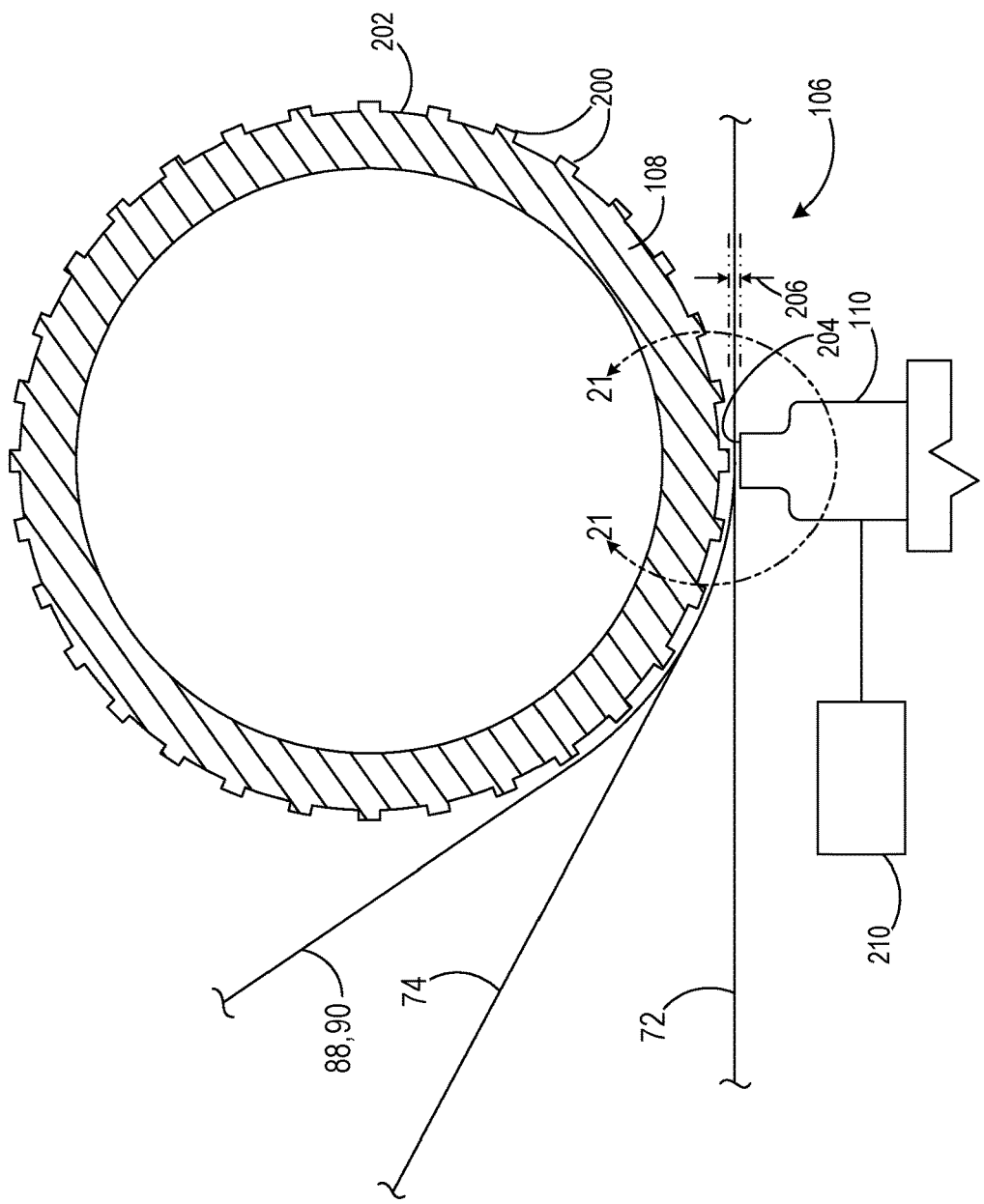

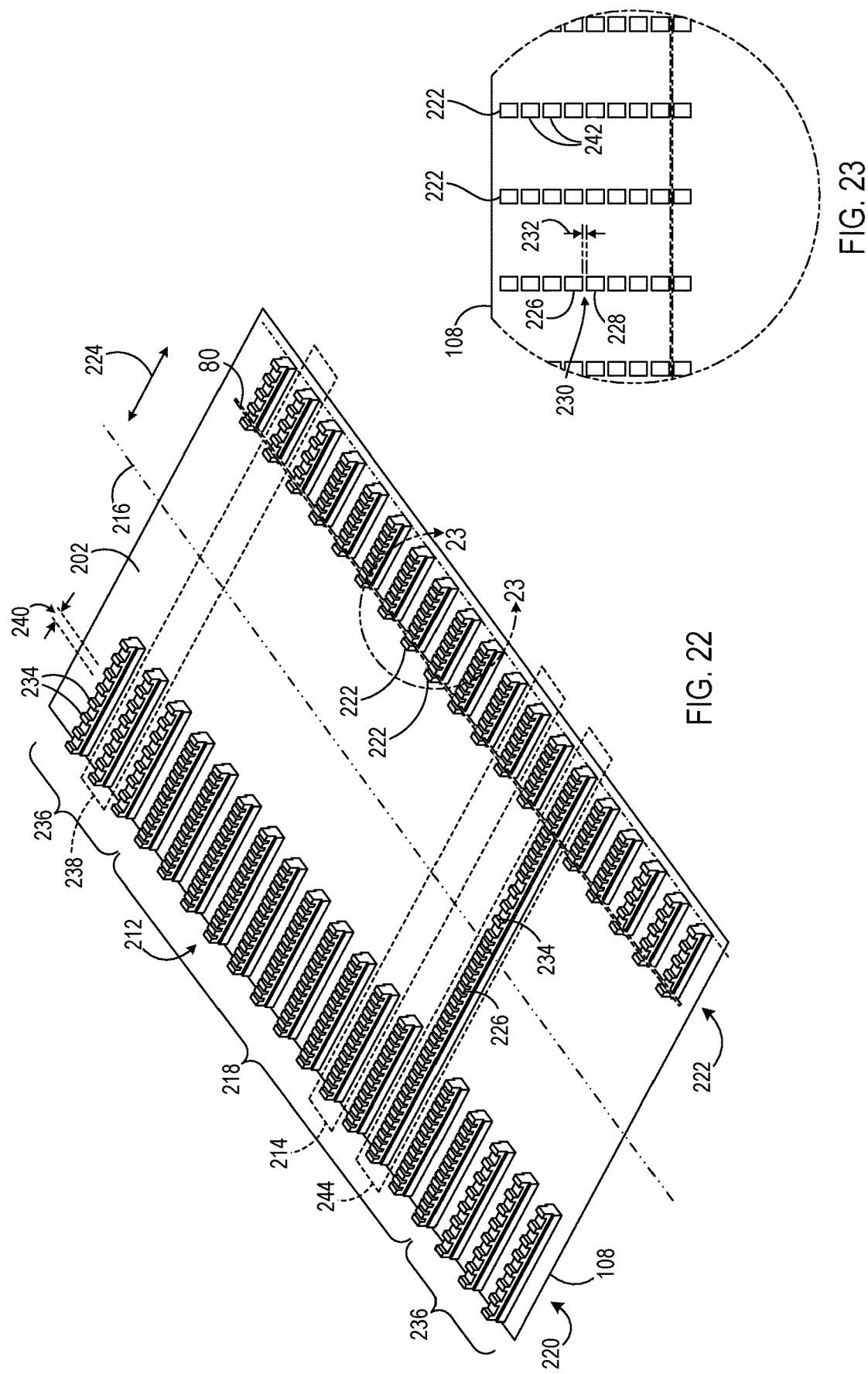

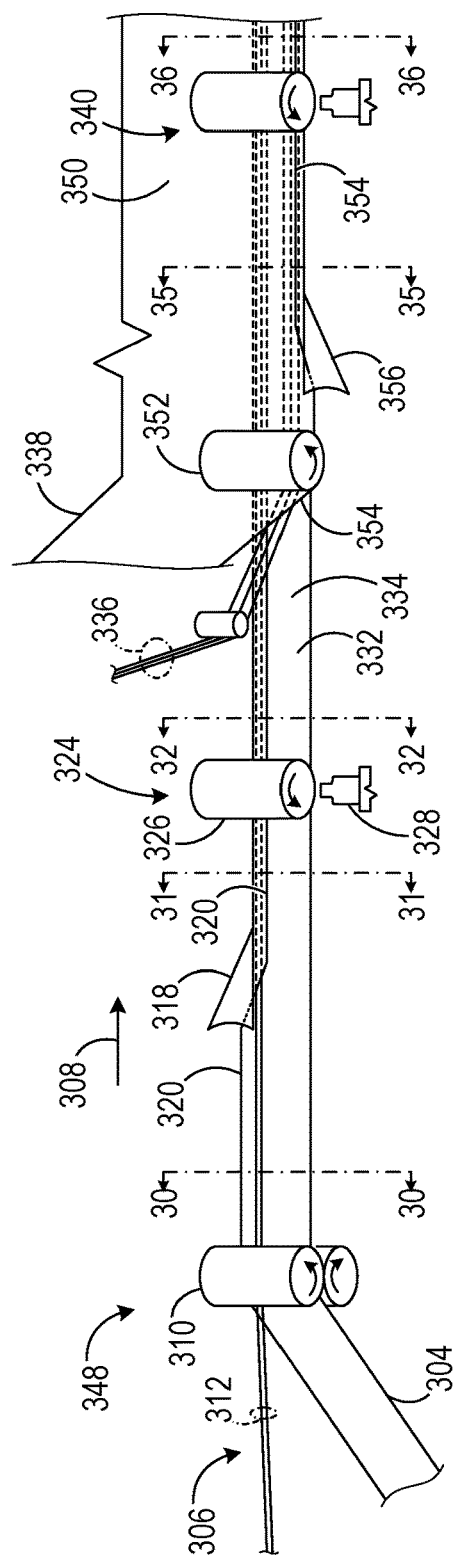
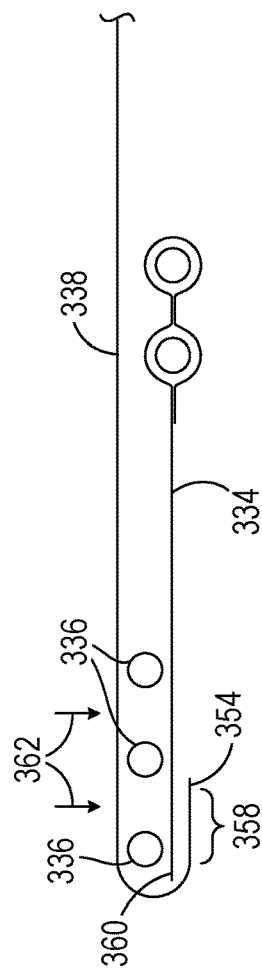
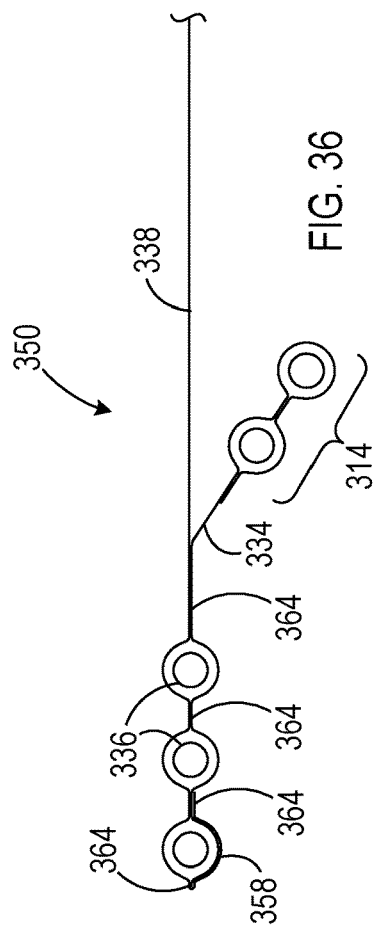
FIG. 34
FIG. 35
FIG. 36

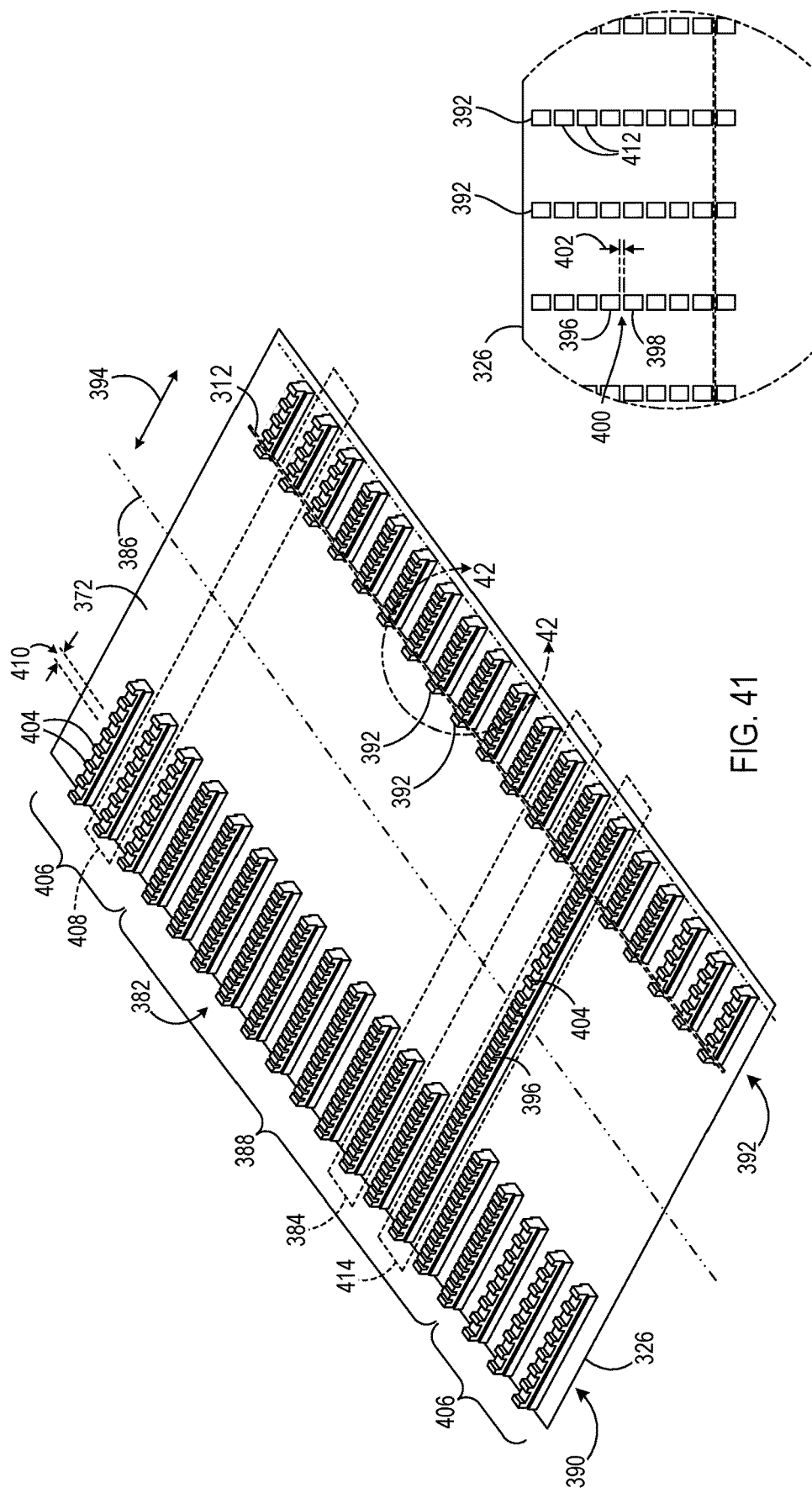

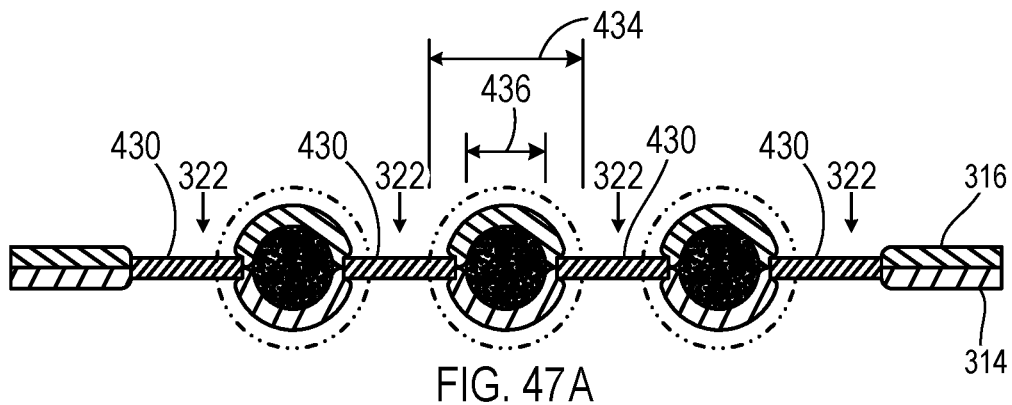
FIG. 47A
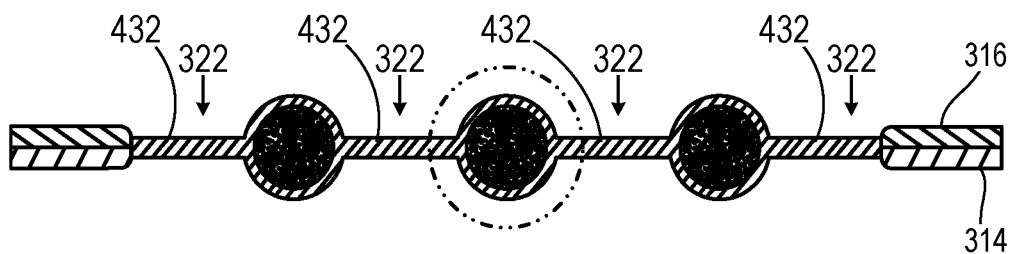
FIG. 47B
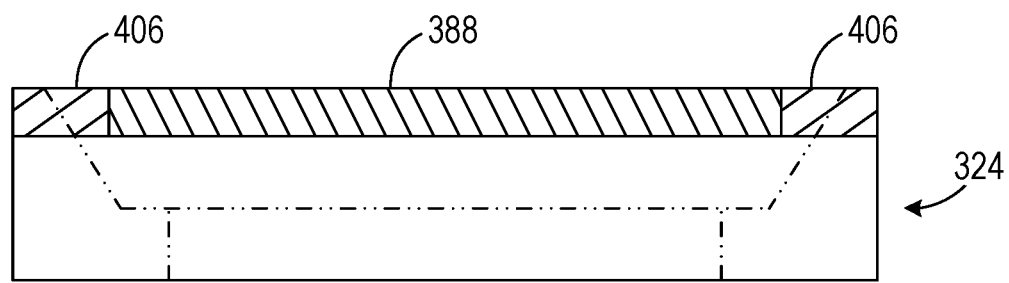
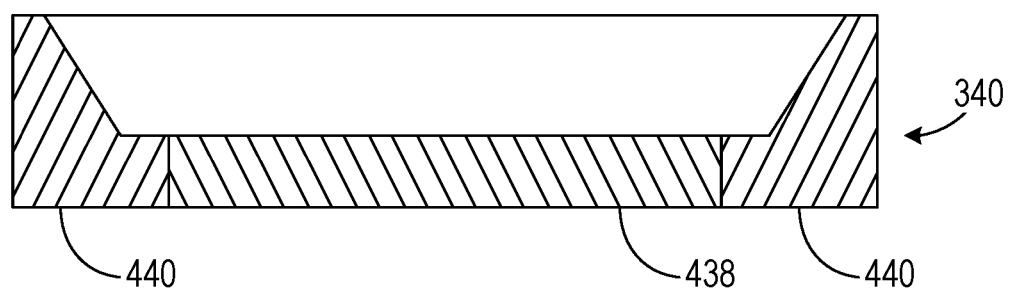
FIG. 48

ELASTIC COMPOSITE STRUCTURE FOR AN ABSORBENT SANITARY PRODUCT AND AN APPARATUS AND METHOD FOR MAKING SAID ELASTIC COMPOSITE STRUCTURE

CROSS-REFERENCE TO RELATED APPLICATIONS

This application is a national phase entry of International Application No. PCT/US2021/070155 filed Feb. 16, 2021 which claims the benefit of priority from U.S. Provisional Application No. 62/977,438 and 62/977,453 filed Feb. 17, 2020. This application incorporates the entire disclosures of all three applications as if they were set forth herein.

BACKGROUND OF THE INVENTION

Embodiments of the invention relate generally to absorbent sanitary products and, more particularly, to an improved apparatus and method for manufacturing an elastic composite structure for use in an absorbent sanitary product that includes forming an elasticized leg and/or leg cuff region that minimizes or eliminates the use of consumable adhesives such as glue.

Absorbent sanitary products, such as disposable diapers or light incontinence products, are typically equipped with elastic composite structures that include one or more elastic threads. These elastic composite structures are positioned at various locations throughout the product, including in the waistbands, leg cuff regions, and throughout all or portions of the front or back panels of the product. FIGS. 1A-D illustrate a method for forming a leg region of a sanitary product having a leg cuff region 2 and a leg elastic region 4 according to one embodiment of a known technique.

FIG. 1A illustrates a plurality of cuff elastics 6 attached to a cuff web 8 via adhesive 10. In FIG. 1B, the cuff web 8 is attached to a topsheet 12 via adhesive 10 at a distal end 14 of the cuff web 8 to allow the leg cuff region 2 freedom of movement independent of the topsheet 12. As shown in phantom, in one embodiment, the cuff web 8 may wrap around the cuff elastics 6 to enclose them within the cuff web 8 to protect the elastics 6 and adhesive 10 from external exposure.

A plurality of leg elastics 16 is adhesively attached to a distal end 18 of a backsheet 20 as illustrated in FIG. 1C. The leg cuff/topsheet assembly of FIG. 1B is adhesively attached to the leg elastic/backsheet assembly of FIG. 1C as illustrated in FIG. 1D. An absorbent core 22 may be positioned between the topsheet 12 and the backsheet 20 prior to securing them together so as to be placed in the space between the sheets 12, 20.

As illustrated in FIGS. 1A-D, the cuff elastics 6 are attached in a separate step than the attachment of the plurality of leg elastics 16. In some cases, the attachment steps of the elastics can have a significant separation upstream/downstream from one another during the manufacturing process.

In addition, in a typical product, the elasticized region formed by the cuff elastics 6 and the plurality of leg elastics 16 does not extend in the machine direction to the waist edges of each product. That is, the elasticized region along the machine direction created by the leg and cuff elastics may not extend to the edge of the waist web portions of the product. Instead, the elasticized region may extend sufficiently to wrap around the leg of an end user of the product while leaving a portion of a waist web free from gathering in the machine direction. In this case, a region free of elastics is desirable in a region of the waist while still maintaining a bond of the topsheet and backsheet together.

The use of adhesives to attach the elastics presents a number of disadvantages in both the end product and manufacturing method, including costs associated with the consumable material, separation of the elastic attachment stages, and undesirable tactile properties of the end product (e.g., stiffness) caused by the adhesives. Accordingly, there is a need for an improved apparatus and method for fabricating an elasticized leg region of the product.

BRIEF STATEMENT OF THE INVENTION

Embodiments of the present invention are directed to a method of attaching elastic strands to a leg and/or cuff web that minimizes or eliminates the use of adhesives, a machine for carrying out that method, and the resulting product.

In accordance with one aspect of the invention, an elastic composite structure includes a first web comprising a leg elastic portion, a leg foldover portion, a cuff elastic portion, and a cuff foldover portion. A leg elastic thread is positioned between the leg elastic portion and the leg foldover portion. A plurality of leg bonds create a respective bond between the leg elastic portion and the leg foldover portion and secure the leg elastic thread therebetween. A cuff elastic thread is positioned between the cuff elastic portion and the cuff foldover portion. A plurality of cuff bonds create a respective bond between the cuff elastic portion and the cuff foldover portion and secure the cuff elastic thread therebetween. The plurality of leg bonds and the plurality of cuff bonds are formed without adhesive.

In accordance with another aspect of the invention, a method of making an elastic composite structure includes positioning a leg elastic thread between a leg elastic portion of a first web and a leg foldover portion of the first web, forming a plurality of leg bonds bonding the leg elastic portion to the leg foldover portion without adhesive, positioning a cuff elastic thread between a cuff elastic portion of the first web and a cuff foldover portion of the first web, and forming a plurality of cuff bonds bonding the cuff elastic portion to the cuff foldover portion without adhesive.

In accordance with another aspect of the invention, an apparatus for forming an elastic composite structure includes a plurality of rollers configured to guide a combined web assembly in a machine direction, where the combined web assembly includes a first web layer comprising a leg elastic portion, a leg foldover portion, a cuff elastic portion, and a cuff foldover portion, at least one leg elastic positioned between the leg elastic portion and the leg foldover portion, and at least one cuff elastic positioned between the cuff elastic portion and the cuff foldover portion. A bonding apparatus having a horn and anvil is configured to bond the leg elastic portion to the leg foldover portion absent adhesive via a plurality of leg bonds and bond the cuff elastic portion to the cuff foldover portion absent adhesive via a plurality of cuff bonds.

In accordance with another aspect of the invention, an elastic composite structure includes a first web having a leg elastic portion, a cuff elastic portion, and a cuff foldover portion. A cuff elastic thread is positioned between the cuff elastic portion and the cuff foldover portion. A plurality of cuff bonds join the cuff elastic portion and the cuff foldover portion and secure the cuff elastic thread therebetween. A second web includes a leg elastic region, a leg elastic thread positioned between the leg elastic portion of the first web and the leg elastic portion of the second web, and a plurality of leg bonds joining the leg elastic portion of the first web and the leg elastic portion of the second web and securing the leg elastic thread therebetween. The plurality of leg bonds and the plurality of cuff bonds are formed without adhesive.

In accordance with another aspect of the invention, a method of making an elastic composite structure includes positioning a cuff elastic thread between a cuff elastic portion of a first web and a cuff foldover portion of the first web, forming a plurality of cuff bonds bonding the cuff elastic portion to the cuff foldover portion without adhesive, positioning a leg elastic thread between a leg elastic portion of the first web and a leg elastic portion of a second web, and forming a plurality of leg bonds bonding the leg elastic portion of the first web and a leg elastic portion of a second web without adhesive.

In accordance with another aspect of the invention, an apparatus for forming an elastic composite structure includes a first plurality of rollers configured to guide a first portion of a combined web assembly in a machine direction, where the first portion of the combined web assembly includes a first web layer comprising a cuff elastic portion and a cuff foldover portion and a plurality of cuff elastics positioned between the cuff elastic portion and the cuff foldover portion. A first bonding apparatus having at least one horn and anvil is configured to bond the cuff elastic portion to the cuff foldover portion absent adhesive via a plurality of cuff bonds that restrain the plurality of cuff elastics relative to the first web layer. A second plurality of rollers is configured to guide a second portion of the combined web assembly in a machine direction, where the second portion of the combined web assembly includes the first web layer comprising a leg elastic portion, a second web layer comprising a leg elastic portion, and a plurality of leg elastics positioned between the leg elastic portion of the first web layer and the leg elastic portion of the second web layer. A second bonding apparatus having at least one horn and anvil configured to bond the leg elastic portion of the first web layer and the leg elastic portion of the second web layer absent adhesive via a plurality of leg bonds that restrain the plurality of leg elastics relative to the first and second web layers.

These and other advantages and features will be more readily understood from the following detailed description of preferred embodiments of the invention that is provided in connection with the accompanying drawings.

BRIEF DESCRIPTION OF THE DRAWINGS

The drawings illustrate embodiments presently contemplated for carrying out the invention.

In the drawings:

FIG. 3 is a schematic view of a portion of a manufacturing line for forming an elasticized leg and leg cuff web assembly according to one embodiment of the invention.

FIG. 4 is a cross-sectional view taken along line 4-4 of FIG. 3.

FIG. 5 is a cross-sectional view taken along line 5-5 of FIG. 3.

FIG. 6 is a cross-sectional view taken along line 6-6 of FIG. 3.

FIG. 7 is a cross-sectional view taken along line 7-7 of FIG. 3.

FIG. 20 is a schematic cross-sectional view of a bonding apparatus that is usable with the manufacturing line of FIG. 3, 8, or 16 according to one embodiment of the invention.

FIG. 21 is a detailed view of a portion of the bonding apparatus of FIG. 20 illustrating the horn aligned with a projection on the rotary anvil, according to one embodiment of the invention.

FIG. 22 is a flattened representation of an exemplary anvil pattern usable with the manufacturing line of FIG. 3, 8, or 16 according to one embodiment of the invention.

FIG. 23 is a detailed view of a portion of the rotary anvil of FIG. 22.

FIG. 34 is a schematic view of a portion of a manufacturing line for forming an elasticized leg and leg cuff web assembly according to another embodiment of the invention.

FIG. 35 is a cross-sectional view taken along line 35-35 of FIG. 34.

FIG. 36 is a cross-sectional view taken along line 36-36 of FIG. 34.

FIG. 41 is a flattened representation of an exemplary anvil pattern usable with the manufacturing line of FIG. 29, 34, or 37 according to one embodiment of the invention.

FIG. 42 is a detailed view of a portion of the rotary anvil of FIG. 41.

FIGS. 47A and 47B are cross-sectional views taken along line 47-47 of FIG. 46.

FIG. 48 is a schematic diagram showing a flattened representation of exemplary anvil patterns showing restraining bond zones and/or lamination bond zones usable with the manufacturing lines of FIG. 29, 34, or 37 according to an embodiment of the invention.

DETAILED DESCRIPTION

Embodiments of the present invention provide for an apparatus and method for forming elasticized cuff and leg regions of an absorbent product such as a disposable product such as a diaper or light incontinence product that reduces or eliminates the use of adhesives such as glue.

Figure 1A:
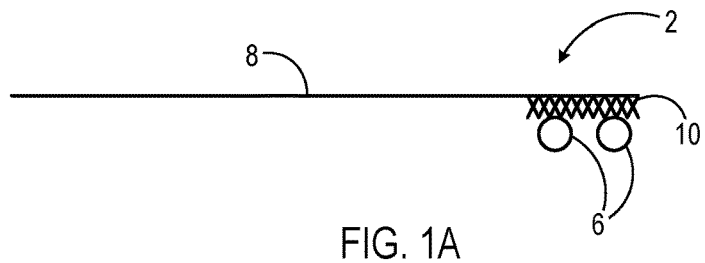
FIGS. 1A-D illustrate a method for forming a leg region of a sanitary product according to one embodiment of a known technique.
Figure 1B:
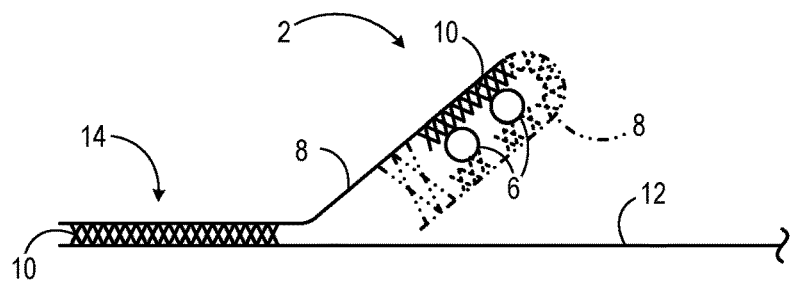
Figure 1C:
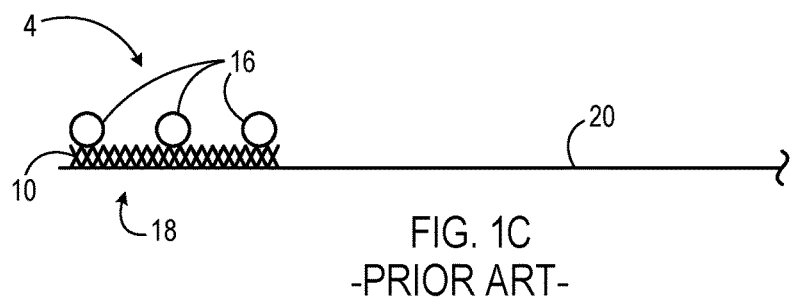
Figure 1D:
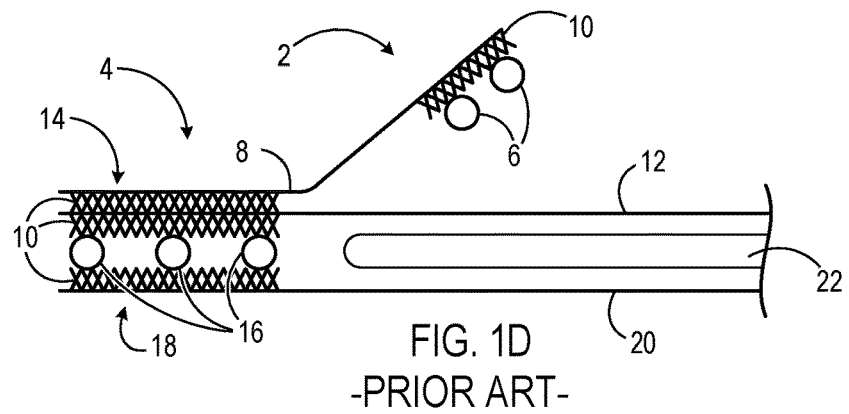
Figure 2:
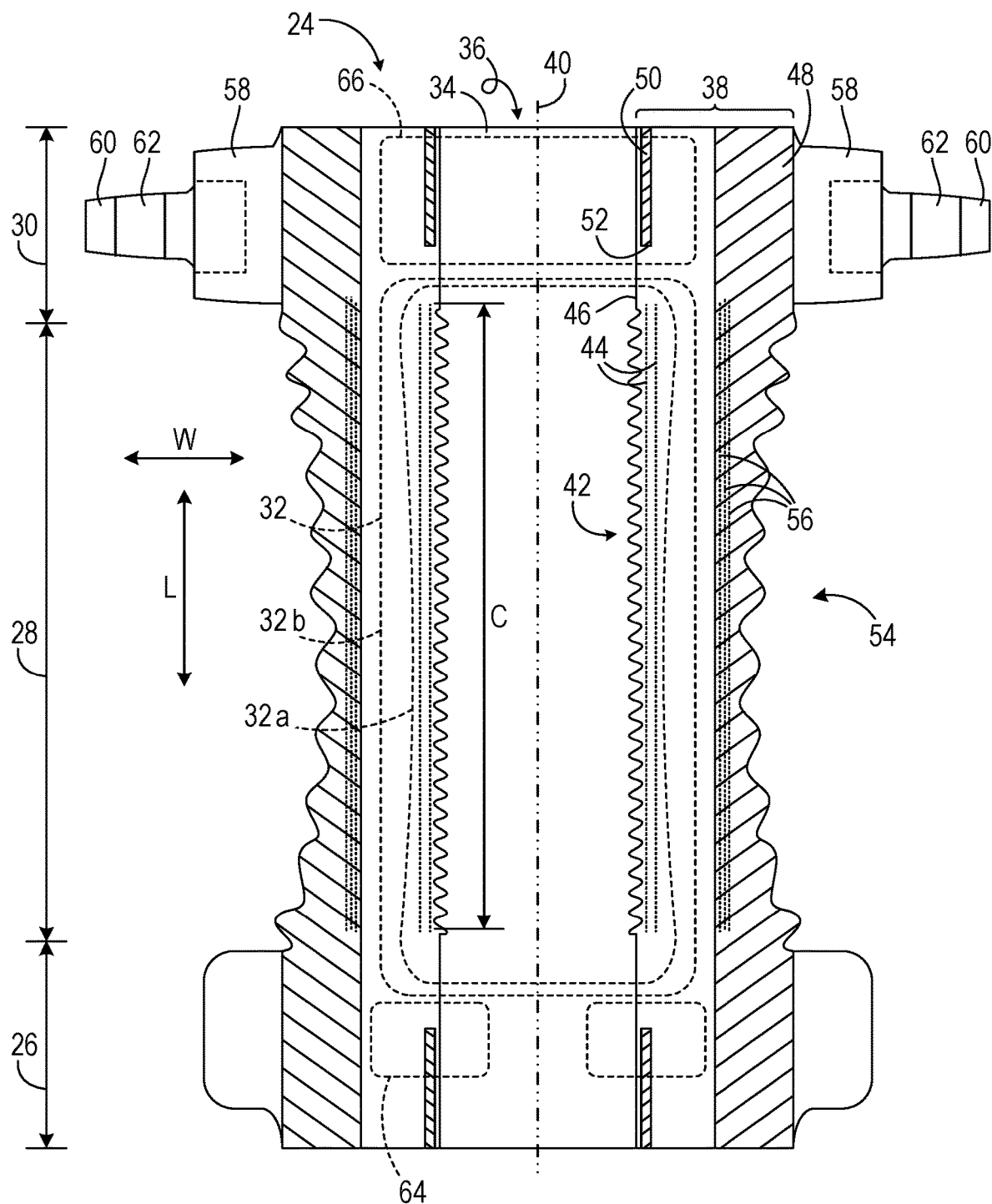
FIG. 2 is a plan view of a sanitary product according to one embodiment of the invention.

FIG. 2 is a plan view of a disposable product 24 according to an exemplary embodiment. The disposable product 24 includes a front waistline region 26, a crotch region 28, and a rear waistline region 30. The front waistline region 26 is a portion coming into contact with a front waistline region (belly portion) of a wearer. The rear waistline region 30 is a portion coming into contact with the rear waistline region (back portion) of the wearer. The crotch region 28 is located between the front waistline region 26 and the rear waistline region 30. In the embodiment shown, a direction from the front waistline region 26 toward the rear waistline region 30 is referred to as a front-back direction L, and a direction orthogonal to the front-back direction L is referred to as a width direction W.

The disposable product 24 includes an absorber 32. The absorber 32 lies across the crotch region 28 and extends toward at least one of the front waistline region 26 and the rear waistline region 30. The illustrated absorber 32 is disposed across the front waistline region 26, the crotch region 28, and the rear waistline region 30. The absorber 32 includes an absorbing core 32a and a core wrap 32b. The absorber 32 may be provided with its own liquid-impermeable back sheet (not illustrated).

A liquid-permeable top sheet 34 is provided and constitutes a skin-facing side of the disposable product 24 and thus comes into contact with the wearer. The top sheet 34 is disposed across the front waistline region 26, the crotch region 28, and the rear waistline region 30. In some embodiments, the top sheet 34 has fibers and may be formed of a non-woven fabric. Alternatively, top sheet 34 may include non-woven materials, woven materials, films, foams, and/or composites or laminates of any of these material types.

A back sheet 36 is provided on a non-skin-facing side of the disposable product 24 opposite the top sheet 34 and is also generally disposed across the front waistline region 26, the crotch region 28, and the rear waistline region 30. In some embodiments, the back sheet 36 has fibers and may be formed of a non-woven fabric. Alternatively, back sheet 36 may include non-woven materials, woven materials, films, foams, and/or composites or laminates of any of these material types.

A pair of side sheets 38 is disposed at least in part along widthwise outer sides of the disposable product 24 and substantially symmetrically with respect to an axis of symmetry 40 extending along the widthwise center of the disposable product 24. In an elasticized region of each side sheet 38, a three-dimensional gather or leg cuff 42 is formed to create an erectile gather capable of rising toward the wearer. The leg cuff 42 is composed of a portion of the side sheet 38 and one or more side resilient members 44 joined thereto. The side resilient members 44 are configured to expand and contract in the front-back direction L and are disposed on inner edge sides of the side sheets 38. The leg cuffs 42 each further include an erectile portion 46 capable of rising toward the wearer, a first fixed portion 48 serving as a starting point edge of erection (rising) of the erectile portion 46, and a second fixed portion 50 located on an outer side of the erectile portion 46 in the front-back direction L and having a first end 52 that serves as a starting point end of rising of the erectile portion 46. A front end edge of the erectile portion 46 matches a rear end edge of the second fixed portion 50 disposed in the front waistline region, and a rear end edge of the erectile portion 46 matches a front end edge of the first fixed portion 48 disposed in the rear waistline region.

The side sheets 38 are joined onto the top sheet 34 at the first fixed portions 48 and the second fixed portions 50. The fixed portions 48, 50 may join the side sheets 38 to the top sheet 34 via joining techniques known in the industry such as ultrasonic, thermal, or pressure bonding techniques that fuse layers of web together, adhesive bonding, or various other forms of welding/joining processes. The erectile portions 46 are provided between the second fixed portions 50 in the front-back direction L without being joined to the top sheet 34 and thus are capable of rising from the top sheet 34. The erectile portions 46 erect toward the wearer in a state in which the side resilient members are contracted. The erectile portions 46 erect toward the wearer in a state in which the disposable product is worn. The erectile portions 46 each include a contracting region C in which the side resilient member 44 is disposed in the contractible manner. The contracting region C is a region where the side resilient members 44 are joined to the side sheets 38 to create an elasticized region. The leg cuffs 42 form walls rising toward the skin-facing side along outer edges of the absorber 32 to prevent exudate from leaking sideward.

On the outer edges of the disposable product 24, leg openings 54 to be placed around the legs of the wearer are formed. The disposable product 24 is provided with one or more leg elastics 56 placed inside the leg openings 54 in the width direction and being capable of expanding and contracting in the front-back direction L.

A pair of cars 58 extend outward of the side sheets 38 in the width direction W in the rear waistline region 30. Ears 58 may be formed from top sheet 34, back sheet 36, side sheet 38, or another sheet attached to the disposable product 24. A pair of fastening tapes 60 extend outward of the cars 58 in the width direction W in the rear waistline region 30. Fastening tapes 60 each have a fastening portion 62 to be fastened to a target portion 64 in the front waistline region 26. The fastening portion 62 is provided with, for example, an engagement hook. The fastening tapes 60 serve to hold the disposable product 24 to the wearer's body by being fastened to target portions 64 in the front waistline region 26. The target portions 64 are provided on a surface of the outer sheet of the front waistline region 26 on the non-skin-facing side. The target portions 64 are configured to catch the engagement hooks of the fastening tapes 60 and function as loops of a hook-and-loop engagement system.

The disposable product 24 includes a waist elastic portion 66 capable of expanding and contracting in the width direction. The waist elastic portion 66 is disposed in the rear waistline region 30. The waist elastic portion 66 is disposed between the pair of fastening tapes 60 and contracts a portion between the fastening tapes 60 in the width direction.

Referring now to FIG. 3, a portion of an exemplary manufacturing line 68 for producing an elasticized leg and leg cuff web assembly 70 is illustrated according to one embodiment of the invention. As shown, a first web layer 72 and a plurality of elastic threads or strands 74 are fed in the machine direction 76 by a roller assembly 78, which may include one or more rollers. Elastic threads 74 includes one or more cuff elastic threads 80 and one or more leg elastic threads 82. The elastic threads 74 travel in the machine direction 76 under tension from a creel assembly (not shown) or similar device. Elastic threads 74 may have any suitable cross-sectional shape that facilitates formation of an elastic composite structure having desired elasticity, visual aesthetic, and manufacturability. As non-limiting examples, elastic threads 74 may have a cross-sectional shape that is round, rectangular, square, or irregular as may be the case where each elastic thread 74 is a multifilament product. The elastic threads 74 may be composed of any suitable elastic material including, for example, sheets, strands or ribbons of thermoplastic elastomers, natural or synthetic rubber, or elastic strands, as non-limiting examples. Each elastic thread 74 may be provided in the form of an individual elastomeric strand or be a manufactured multifilament product that includes many individual elastomeric filaments joined together, such as by a dry-spinning manufacturing process, to form a single, coalesced elastic thread 74.

Referring to FIG. 4, a cross-sectional view taken along line 4-4 of FIG. 3 is illustrated. First web layer 72 includes a cuff elastic portion 84 configured to receive the cuff elastic threads 80 and a leg elastic portion 86 configured to receive the leg elastic threads 82. In addition, first web layer 72 includes a cuff foldover portion 88 configured to be folded over at least the cuff elastic threads 80 and the cuff elastic portion 84 and includes a leg foldover portion 90 configured to be folded over at least the leg elastic threads 82 and the leg elastic portion 86.

Referring back to FIG. 3, first web layer 72 and elastic threads 74 travel downstream to a folding assembly 92 having, for example, a pair of plow folders 94, 96, although it is to be understood that alternative types of known folding structures may be used. Plow folder 94 is configured to fold over the cuff foldover portion 88 of first web layer 72 so as to overlap at least the cuff elastic threads 80. In one embodiment, the length of cuff foldover portion 88 may extend so as to also overlap a portion of the leg elastic portion 86. During folding, a cuff edge 98 of first web layer 72 is moved away from being an outside edge of the first web layer 72 on the cuff elastic side of the elasticized leg and leg cuff web assembly 70. Plow folder 96 is configured to fold over the leg foldover portion 90 of first web layer 72 so as to overlap at least the leg elastic threads 82 and the leg elastic portion 86 and may extend to overlap a portion of the cuff elastic portion 84 as well. During folding, a leg edge 100 of first web layer 72 is moved away from being an outside edge of the first web layer 72 on the leg elastic side of the elasticized leg and leg cuff web assembly 70.

As illustrated in the cross-section view of FIG. 5 taken along line 5-5 of FIG. 3, foldover portions 88, 90 respectively overlap the cuff and leg elastic portions 84, 86 after the folding. A plurality of leg bonding sites 102 and cuff bonding sites 104 are available for bonding the cuff and leg elastic portions 84, 86 to the foldover portions 88, 90 as described below.

Referring back to FIG. 3, downstream of the folding assembly 92, a bonding apparatus 106 is positioned to receive the assembly of the first web layer 72 with folded portions about the elastic threads 74 to bond the cuff and leg elastic portions 84, 86 to the foldover portions 88, 90 at the bonding sites 102. Bonding apparatus 106 may be any known ultrasonic welding system in alternative embodiments, including, as non-limiting examples, a rotary ultrasonic welding system or a blade ultrasonic welding system. In the illustrated embodiment, bonding apparatus 106 includes a rotary anvil 108 and an ultrasonic fixed blade horn 110, also known as a sonotrode, which cooperate with each other to bond (i.e., fuse) the cuff and leg elastic portions 84, 86 to the foldover portions 88, 90. Alternative embodiments may include multiple fixed blade horns or one or more rotary horns. As illustrated in the cross-section view of FIG. 6 taken along line 6-6 of FIG. 3, during the bonding process, the elastic threads 80, 82 may be secured in position relative to the first web layer 72 by leg bonds 112 and cuff bonds 114 to create elasticized regions of the elasticized leg and leg cuff web assembly 70 or may be unsecured by the bonds 112, 114 so as to freely move independently of the first web layer 72 in non-elasticized regions of the elasticized leg and leg cuff web assembly 70.

The ultrasonic emission of energy from bonding apparatus 106 is concentrated at specific bond points where frictional heat fuses the layers of web together without the need for consumable adhesives. While bonding apparatus 106 is described herein as an ultrasonic bonding assembly that ultrasonically fuses layers of web together, it is contemplated that the techniques described herein may be extended to any other known welding or bonding techniques that fuse together two or more material layers without the use of adhesive, including ultrasonic, thermal, or pressure bonding techniques and various other forms of welding known in the industry.

As shown in FIG. 3, after the bonding by the bonding apparatus 106, an adhesive applicator 116 applies adhesive 118 (FIG. 7) to the leg elastic portion of the elasticized leg and leg cuff web assembly 70 to adhesively join the elasticized leg and leg cuff web assembly 70 to a second web layer 120 such as a topsheet using a roller assembly 122 configured to apply pressure to press or join the elasticized leg and leg cuff web assembly 70 and the second web layer 120 together. As illustrated in FIG. 7, the adhesively joined assembly provides an elasticized leg region 124 with an elasticized cuff region 126 when combined into a finished product such as a disposable diaper or light incontinence product.

Figure 8:
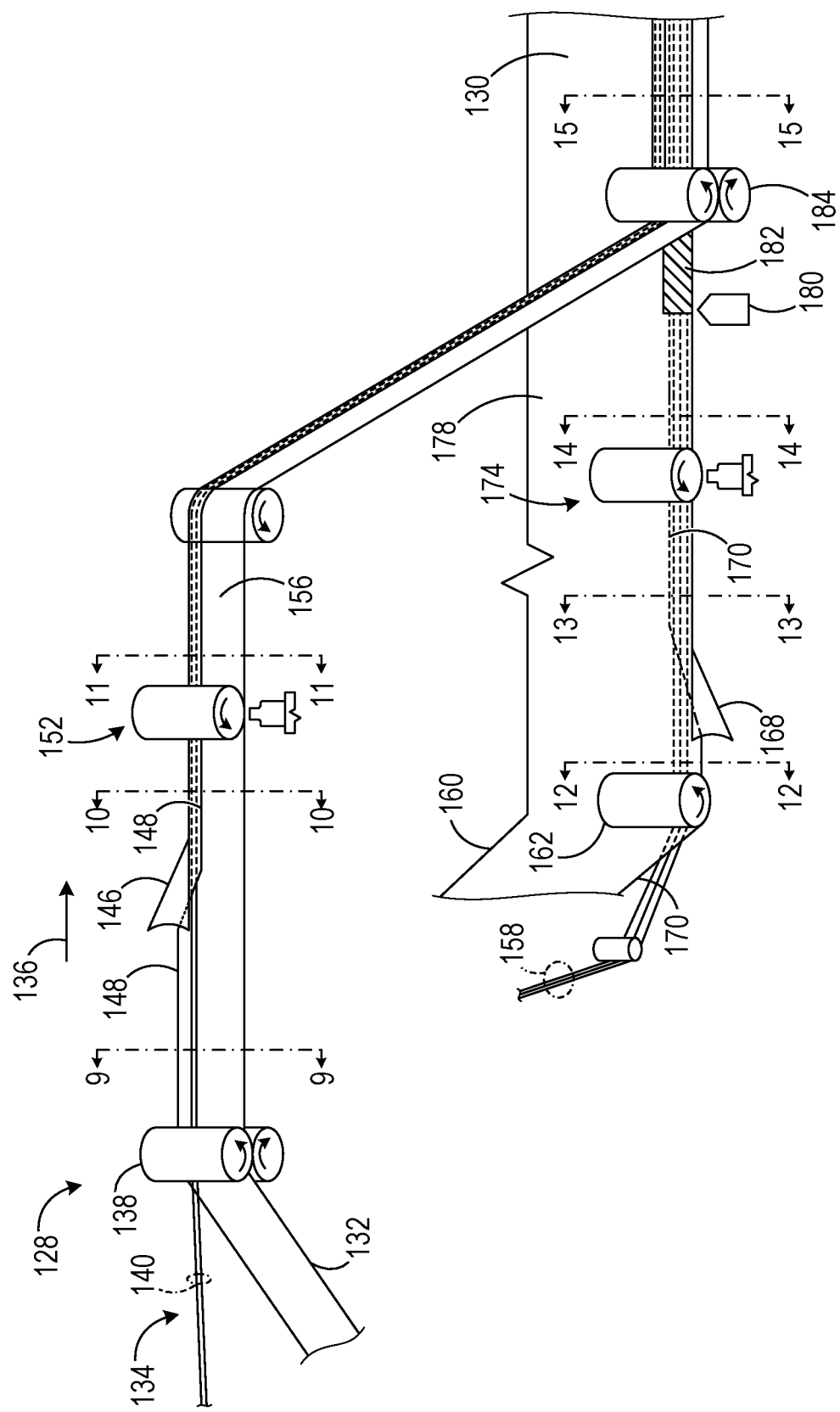
FIG. 8 is a schematic view of a portion of a manufacturing line for forming an elasticized leg and leg cuff web assembly according to another embodiment of the invention.

Referring now to FIG. 8, a portion of an exemplary manufacturing line 128 for producing an elasticized leg and leg cuff web assembly 130 is illustrated according to another embodiment of the invention. As shown, a first web layer 132 and a plurality of elastic threads or strands 134 are fed in the machine direction 136 by a roller assembly 138, which may include one or more rollers. In the illustrated embodiment, elastic threads 134 includes a group of cuff elastic threads 140. Alternative embodiments may include a single elastic thread 134. The elastic threads 134 travel in the machine direction 136 under tension from a creel assembly (not shown) or similar device. Elastic threads 134 may have any suitable cross-sectional shape that facilitates formation of an elastic composite structure having desired elasticity, visual aesthetic, and manufacturability. As non-limiting examples, elastic threads 134 may have a cross-sectional shape that is round, rectangular, square, or irregular as may be the case where each elastic thread 134 is a multifilament product. The elastic threads 134 may be composed of any suitable elastic material including, for example, sheets, strands or ribbons of thermoplastic elastomers, natural or synthetic rubber, or elastic strands, as non-limiting examples. Each elastic thread 134 may be provided in the form of an individual elastomeric strand or be a manufactured multifilament product that includes many individual elastomeric filaments joined together, such as by a dry-spinning manufacturing process, to form a single, coalesced elastic thread 134.

Figure 9:
FIG. 9 is a cross-sectional view taken along line 9-9 of FIG. 8.

Referring to FIG. 9, a cross-sectional view taken along line 9-9 of FIG. 8 is illustrated. First web layer 132 includes a cuff elastic portion 142 configured to receive the cuff elastic threads 140. In addition, first web layer 132 includes a cuff foldover portion 144 configured to be folded over at least the cuff elastic threads 140 and the cuff elastic portion 142.

Referring back to FIG. 8, the first web layer 132 and elastic threads 134 travel downstream to a folding assembly 146 having a plow folder or other known folding apparatus. Folding assembly 146 is configured to fold over the cuff foldover portion 144 of the first web layer 132 so as to overlap at least the cuff elastic threads 140. During folding, a cuff edge 148 of first web layer 132 is moved away from being an outside edge of the first web layer 132 on the cuff elastic side of the first web layer 132.

Figure 10:
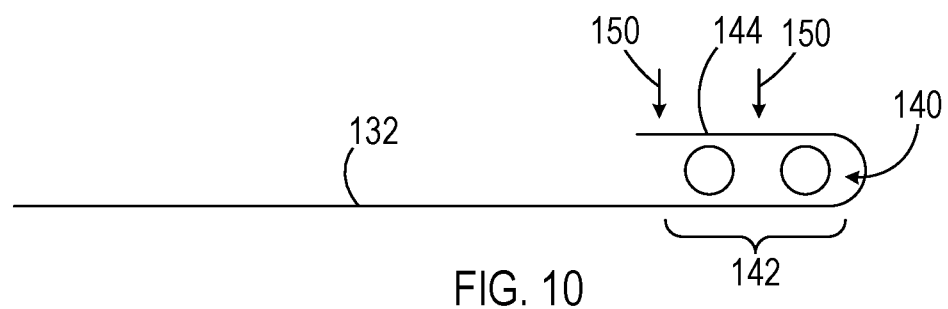
FIG. 10 is a cross-sectional view taken along line 10-10 of FIG. 8.

As illustrated in the cross-sectional view of FIG. 10 taken along line 10-10 of FIG. 8, foldover portion 144 overlaps the cuff elastic portion 142 after the folding. A plurality of cuff bonding sites 150 are available for bonding the cuff elastic portion 142 to the foldover portion 144 as described below.

Referring back to FIG. 8, downstream of the folding assembly 146, a bonding apparatus 152 is positioned to receive the assembly of the first web layer 132 with folded portions about the elastic threads 134 to bond the cuff elastic portion 142 to the foldover portion 144 at the bonding sites 150. Bonding apparatus 152 may be similar to the bonding apparatus 106 described herein.

Figure 11:
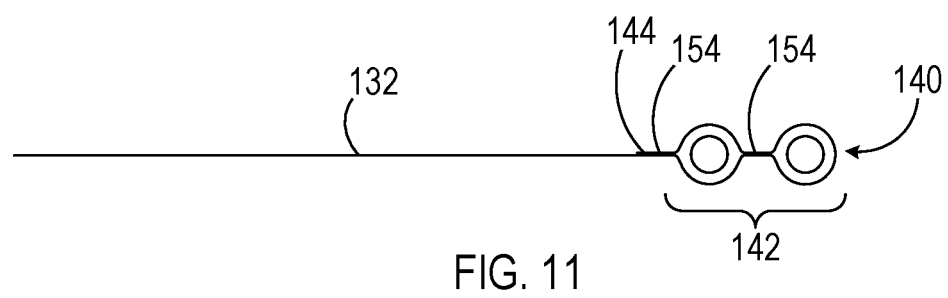
FIG. 11 is a cross-sectional view taken along line 11-11 of FIG. 8.

As illustrated in the cross-section view of FIG. 11 taken along line 11-11 of FIG. 8, during the bonding process, the elastic threads 140 may be secured in position relative to the first web layer 132 by cuff bonds 154 to create elasticized regions of the elasticized leg and leg cuff web assembly 130 or may be unsecured by the bonds 154 so as to freely move independently of the first web layer 132 in non-elasticized regions of the elasticized leg and leg cuff web assembly 130. After the bonding by the bonding apparatus 152, an elasticized cuff web 156 is provided for further processing downstream.

As shown in FIG. 8, in a separate portion of the manufacturing line 128, one or more leg elastic threads 158 and a second web layer 160 such as a topsheet are fed in the machine direction 136 by a roller assembly 162, which may include one or more rollers. The leg elastic threads 158 may be similar to or distinct from the cuff elastic threads 140.

Figure 12:
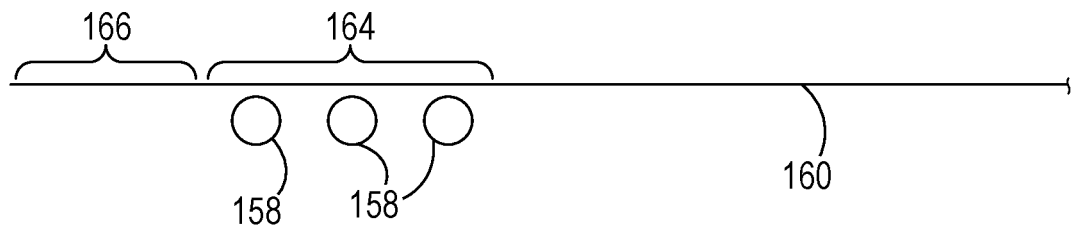
FIG. 12 is a cross-sectional view taken along line 12-12 of FIG. 8.

As illustrated in FIG. 12 taken along line 12-12 of FIG. 8, second web layer 160 includes a pair of leg elastic portion 164 configured to receive the leg elastic threads 158. In addition, second web layer 160 includes a leg foldover portion 166 configured to be folded over at least the leg elastic threads 158 and the leg elastic portion 164.

Referring back to FIG. 8, the second web layer 160 and elastic threads 134 travel downstream to a folding assembly 168 having a plow folder or other known folding apparatus. Folding assembly 168 is configured to fold over the leg foldover portion 166 of the second web layer 160 so as to overlap at least the leg elastic threads 158. During folding, a leg edge 170 of second web layer 160 is moved away from being an outside edge of the second web layer 160 on the leg elastic side of the second web layer 160.

Figure 13:
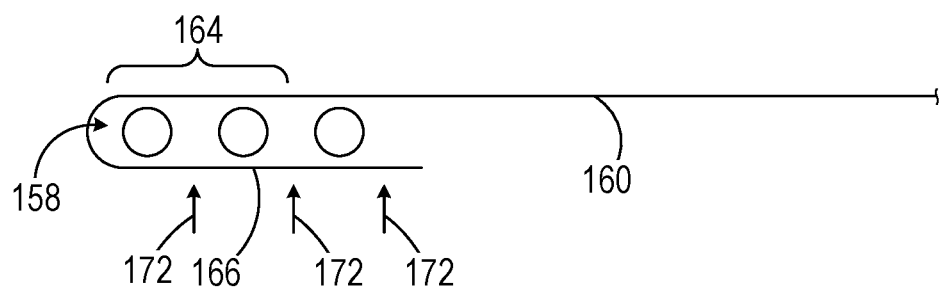
FIG. 13 is a cross-sectional view taken along line 13-13 of FIG. 8.

As illustrated in the cross-sectional view of FIG. 13 taken along line 13-13 of FIG. 8, leg foldover portion 166 overlaps the leg elastic portion 164 after the folding. A plurality of leg bonding sites 172 are available for bonding the leg elastic portion 164 to the leg foldover portion 166 as described below.

Referring back to FIG. 8, downstream of the folding assembly 168, a bonding apparatus 174 is positioned to receive the assembly of the second web layer 160 with folded portions about the leg elastic threads 158 to bond the leg elastic portion 164 to the leg foldover portion 166 at the bonding sites 172. Bonding apparatus 174 may be similar to the bonding apparatus 106 described herein.

Figure 14:
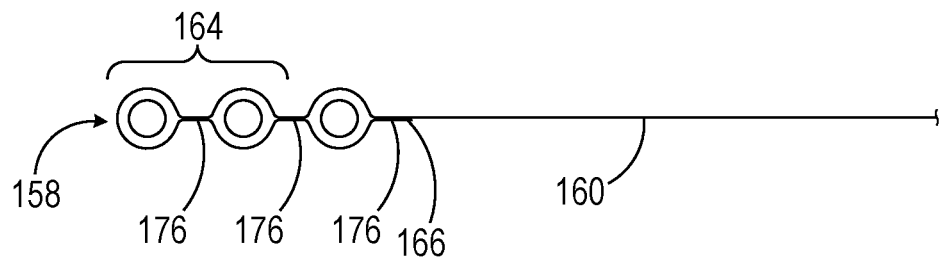
FIG. 14 is a cross-sectional view taken along line 14-14 of FIG. 8.

As illustrated in the cross-section view of FIG. 14 taken along line 14-14 of FIG. 8, during the bonding process, the leg elastic threads 158 may be secured in position relative to the second web layer 160 by leg bonds 176 to create elasticized regions of the elasticized leg and leg cuff web assembly 130 or may be unsecured by the bonds 176 so as to freely move independently of the first web layer 132 in non-elasticized regions of the elasticized leg and leg cuff web assembly 130. After the bonding by the bonding apparatus 152, an elasticized leg web 178 is provided for further processing downstream.

As shown in FIG. 8, after the bonding by the bonding apparatus 174, an adhesive applicator 180 applies adhesive 182 to the leg elastic portion 164 of the elasticized leg web 178. Thereafter, a roller assembly 184 receives both the elasticized leg web 178 and the elasticized cuff web 156 to applies pressure to adhesively join them together to form the elasticized leg and leg cuff web assembly 130, which may be used in a finished product such as a disposable diaper or light incontinence product.

Figure 15:
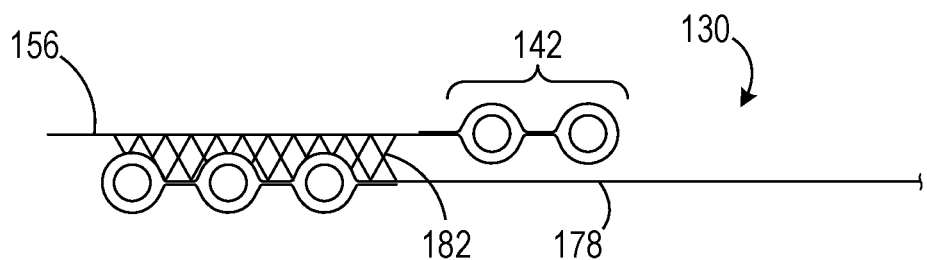
FIG. 15 is a cross-sectional view taken along line 15-15 of FIG. 8.

As illustrated in the cross-section view of FIG. 15 taken along line 15-15 of FIG. 8, the elasticized leg web 178 and the elasticized cuff web 156 are adhesively joined while leaving the cuff elastic portion 142 with freedom of movement independent of the elasticized leg web 178.

Figure 16:
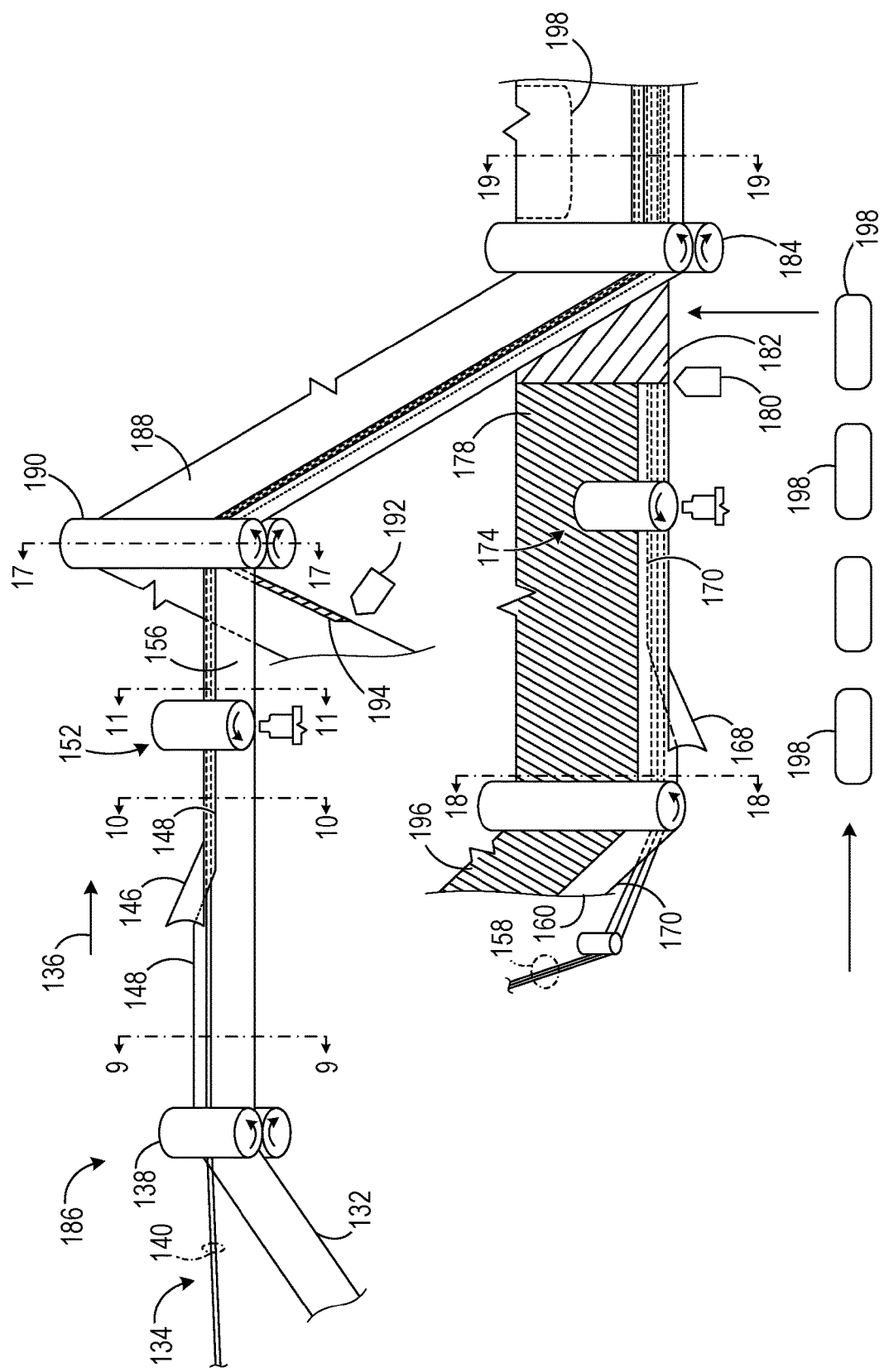
FIG. 16 is a schematic view of a portion of a manufacturing line for forming an elasticized leg and leg cuff web assembly according to another embodiment of the invention.

FIG. 16 illustrates a portion of an exemplary manufacturing line 186 for producing the elasticized cuff web 156 and the elasticized leg web 178 according to another embodiment of the invention. A first portion of manufacturing line 186 is similar to that described in FIGS. 8-11, and similar portions that are numbered identically and not described or referenced below are as described above and, for simplicity, will not be repeated.

Figure 17:
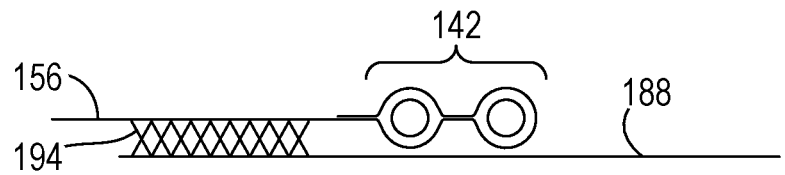
FIG. 17 is a cross-sectional view taken along line 17-17 of FIG. 16.

Downstream of bonding apparatus 152, the elasticized cuff web 156 is joined together with a topsheet 188 via a roller assembly 190. An adhesive applicator 192 applies adhesive 194 near an edge of the topsheet 188 that joins the elasticized cuff web 156 to the topsheet 188 in response to the pressure applied by the roller assembly 190. The adhesively-joined web/topsheet assembly is provided for further processing downstream. FIG. 17 is a cross-sectional view taken along line 17-17 of FIG. 16 and illustrates the elasticized cuff web 156 adhesively bonded to the topsheet 188.

Figure 18:
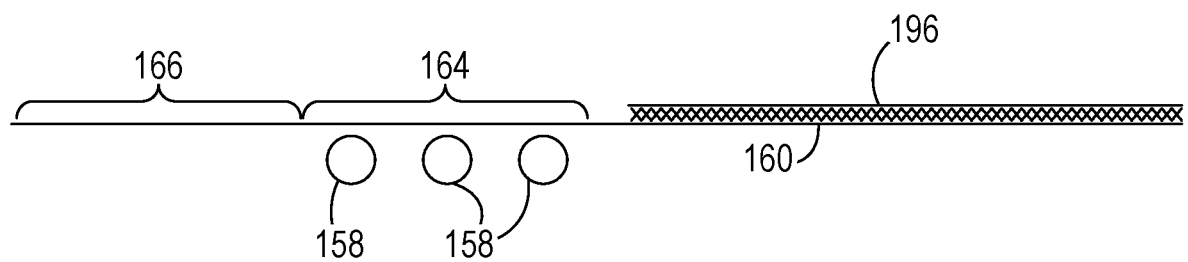
FIG. 18 is a cross-sectional view taken along line 18-18 of FIG. 16.

A backsheet film 196 that serves to provide an impermeable layer adjacent to the second web layer 160 is adhesively attached to the second web layer 160 is illustrated in FIGS. 16 and 18. The adhesive 182 in the manufacturing line 186 is applied to the elasticized leg web 178 in a greater quantity than described with respect to FIG. 8. A plurality of absorbent cores 198 is schematically illustrated, and each absorbent core 198 is inserted between the elasticized cuff web 156 and the elasticized leg web 178 prior to their adhesive bonding by roller assembly 184 as the webs travel in the machine direction 136 in one embodiment.

Figure 19:
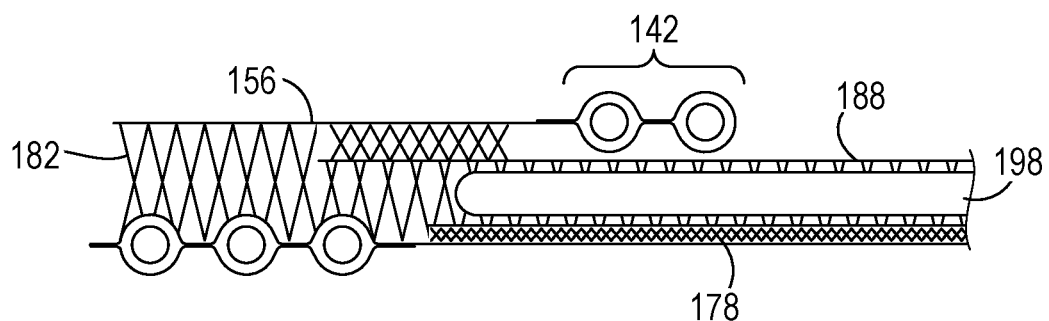
FIG. 19 is a cross-sectional view taken along line 19-19 of FIG. 16.

As illustrated in the cross-section view of FIG. 19 taken along line 19-19 of FIG. 16, the elasticized leg web 178 and the elasticized cuff web 156 are adhesively joined with the absorbent core 198 therebetween while leaving the cuff elastic portion 142 with freedom of movement independent of the elasticized leg web 178.

Referring now to FIG. 20, anvil 108 is illustrated according to one embodiment of the invention. As shown, the anvil 108 includes an arrangement of discrete projections 200 that extend outward from the anvil face 202. These projections 200 are constructed to (A) fuse together first web layer 72 to cuff foldover portion 88 and first web layer 72 to leg foldover portion 90 and (B) restrain or hold the elastic threads 74 in position relative to the bonded layers in the manufactured elastic composite structure 70. As described in more detail below, restraining projections 200 are designed so that an elastic thread 74 that passes between two adjacent restraining projections 200 on the face 202 of anvil 108 is restrained in position relative to the bonded layers by frictional resistance that prevents the elastic thread 74 from sliding through the pair of resulting bonds.

The particular size, shape, and general arrangement of restraining projections 200 as well as the total number of projections 200 illustrated in FIG. 20 are intended to depict a representative and non-limiting example of an overall pattern of projections 200 on anvil 108. Alternative embodiments may include any number of projections 200 arranged in any number of alternative configurations to achieve a desired pattern of bonds on the end product. The respective working surfaces of restraining projections 200 may be configured to form bonds of similar size and shape, or bonds of different size and/or shape in alternative embodiments. As non-limiting examples, respective land surfaces of restraining projections 200 may be circular, rectangular, crescent shaped, or have irregular shapes that may be selected to form a desired overall pattern on the end product. The resulting pattern of bonds will include one or more restrained zones, which fix or anchor one or more elastic threads 74 under tension in position relative to the bonded layers.

In a preferred embodiment, the restraining projections 200 are formed on anvil 108 using a machining process that removes bulk material from the anvil 108 to create the desired raised pattern of projections 200 relative to the face 202 of the anvil 108. Alternatively, restraining projections 200 may be provided on one or more inserts that are mechanically coupled to the face 202 of the anvil 108.

Still referring to FIG. 20, the working surface 204 of the horn 110 has a smooth or substantially smooth surface contour in one non-limiting embodiment. Alternatively, working surface 204 may include an arrangement of projections 200 and/or grooves that mate or align with the pattern of projections 200 on the anvil 108 to further facilitate fusing the one web layer to another web layer and securing the elastic threads 74 in position relative to fused layers.

During the manufacturing process, the layers to be fused are positioned between the face 202 of the anvil 108 and the working surface 204 of the horn 110 as shown in FIG. 20. Elastic threads 74 are positioned between the fusible layers in a tensioned state. As generally shown in FIG. 20 and in further detail in FIG. 21, the position of horn 110 is controlled to maintain a nip gap 206 between the working surface 204 of horn 110 and the land surfaces 208 of the restraining projections 200. The size of the nip gap 206 is determined based on parameters of the manufacturing process to facilitate bonding between the fusible layers. Bonding apparatus 106 may include any known positioning means 210 that exerts a force on at least one of the horn 110 and anvil 108 to maintain a desired nip gap 206 between the horn 110 and anvil 108. Positioning means 210 may be an air pressure assembly (not shown) or a mechanical camshaft (not shown) as non-limiting examples.

Restraining projections 200 may have a planar working surface, planar side surfaces, or some mixture of curved and straight working and side surfaces in alternative embodiments. In the embodiment illustrated in FIG. 21, the land surface 208 of restraining projection 200 has planar working and side surfaces. In alternative embodiments where the land surface 208 has an arced or curved surface profile, this curved profile permits the fusible layers to slip relative to the face 202 of the anvil 108 during the bonding process and thus allows the velocity at which the combined assembly of the tensioned elastic strands 74 and fusible layers is advanced toward the bonding apparatus 106 to be increased or decreased relative to the rotational velocity of the anvil 108. When the combined web/thread assembly is advanced at a velocity greater than the velocity of the anvil 108, the resulting bonds are spaced apart by a distance greater than the radial spacing between adjacent projections 200 on the anvil face 202. Similarly, slowing the feed rate of the combined web/thread assembly relative to the velocity of the anvil 108 will result in bonds that are spaced apart by a distance less than the radial spacing between adjacent projections 200 on the anvil face 202. The velocity mismatch or differential between web speed and anvil velocity can be controlled to accommodate size changes in the end product. As a result, the bonding of an elastic composite for one size diaper may be carried out with little or no slip, while the bonding of an elastic composite for a larger or smaller diaper may be carried out with a larger amount of slip. A manufacturing line of FIG. 3, 8, or 16 outfitted with an anvil that includes projections 200 with curved surface profiles thus provides for dynamic size changing without having to change the tooling set-up of the manufacturing line, as the same anvil can be used to manufacture multiple sizes of elastic composite structures for use in different sized products.

FIG. 22 is a flattened representation of the circumferential face 202 of anvil 108 according to an embodiment where anvil 108 includes a pattern of projections 212 that form restrained zones. The pattern of projections 212 includes multiple restraining weld lines 214 that are spaced apart from one another along the circumferential axis 216 of the anvil face 202. The restraining weld lines 214 define one or more restraining regions 218 of the projection pattern 212. As with restraining projections 200 above, in a preferred embodiment, the restraining weld lines 214 are formed on anvil 108 using a machining process that removes bulk material from the anvil 108 to create the desired raised pattern of restraining weld lines 214 relative to the face 202 of the anvil 108. Alternatively, restraining weld lines 214 may be provided on one or more inserts that are mechanically coupled to the face 202 of the anvil 108.

FIG. 22 illustrates restraining weld lines 214 having separate welding line portions 220, 222 on opposite sides of the face 202 along the longitudinal direction 224 of the rotary anvil 108. The longitudinal direction 224 generally extends in the cross-machine direction. The spacing between adjacent restraining weld lines 214 as well as the length and placement of each restraining weld line 214 along the longitudinal direction 224 may be subject to the design of the bond pattern desired in the finished product.

As shown more specifically in the detailed view provided in FIG. 23, each weld line 214 contains a pattern of discrete projections 226, 228 that extend outward away from the face 202 of the anvil 108. The projections 226, 228 are spaced apart from one another, by a notch 230 that is defined by the width of a gap 232 positioned between a given pair of adjacent projections 226, 228. The width or size of the gap 232 may restrain one or more elastic threads 74 between adjacent bonds formed by projections 226, 228 such that the elastic thread(s) 74 is held tightly by and between the adjacent bonds. In this manner, for example, the adjacent bonds constrain the elastic thread(s) 74 such that the elastic thread(s) 74 is restrained between the adjacent bonds to create an elasticized region absent the use of adhesives. Elasticized regions are formed by the projections in the restraining region section 218 of the rotary anvil 108.

Anvil 108 may in addition or alternatively include one or more projections that are referred to herein as lamination or non-restraining projections 234. As illustrated in FIG. 22, a plurality of lamination projections 234 are shown in one or more lamination portions 236 of the rotary anvil 108 in lamination weld lines 238. Lamination projections 234, similar to the restraining or restraining projections 226, 228, fuse first and second web layers 72, 120 to one another. Lamination projections 234 differ from restraining projections 226, 228 because they do not restrain the elastic threads 74 in position relative to the fused web layers due to the spacing of the gap 240 between adjacent projections 226, 228. Accordingly, a broken elastic thread 74 is free to contract out of the gap between the adjacent lamination weld bonds if the length of the contraction is sufficient. Such lamination projections 234 are advantageous, for example, when laminating the two web layers in areas designed for elastic deactivation in which the elastic threads 74 are purposely broken in order to create a non-elastic portion of the bonded web layers. Embodiments of the invention contemplate the use or non-use of any number and placement of the lamination projections 234.

Referring to FIG. 23, it is contemplated that the contact surfaces 242 of the projections 226, 228 may have different geometries in alternative embodiments. As non-limiting examples, projections 226, 228 may be circular, rectangular, crescent shaped, or have irregular shapes that may be selected to form a desired overall pattern on the end product. In yet another embodiment, corresponding projections 226, 228 of adjacent weld lines 214 may be aligned with one another in a line parallel to the circumferential axis 216. Alternatively, projections 226, 228 of sequential weld lines 214 may be offset from one another in the cross-machine direction thereby defining a stepped or non-linear passage through the bond lines that are formed on the fused web layers.

Referring again to FIG. 22, an alternative weld line 244 is illustrated as an example to show another embodiment in which a weld line extends a majority of the width of the anvil 108 in the longitudinal direction 224. As shown, restraining weld line 244 includes both restraining projections 226 and lamination projections 234. The combination of projections 226, 234 may also be designed into any of the other weld lines 214, 238 as well. Alternatively, weld line 244 may include only one of the types of projections 226, 234 in other embodiments.

FIGS. 22 and 23 illustrate an elastic thread (such as cuff elastic thread 80) in phantom in a stretched state extending between adjacent restraining projections 226 and/or 228 of restraining weld lines 214 and between adjacent lamination projections 234 of lamination weld lines 238. The restraining bonds (illustrated in FIG. 27) formed by adjacent restraining projections 226, 228 may form separate, independent bonds spaced apart by a distance less than the diameter or width of the un-stretched elastic thread or may form a single bond across the elastic thread from one contact surface 242 to the other contact surface 242 on the other side of the elastic thread.

Figure 24:
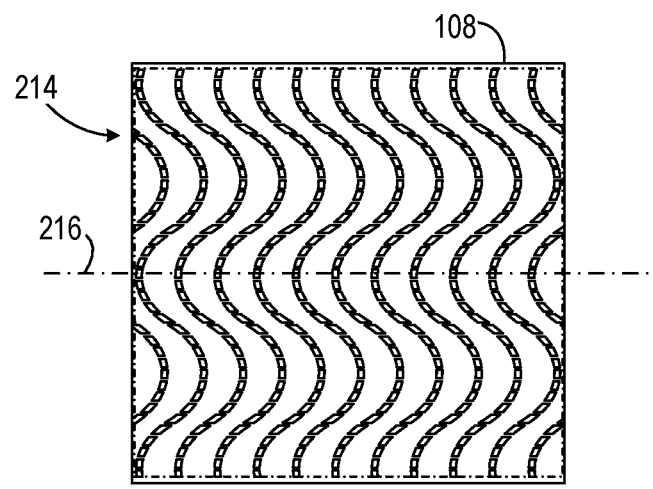
FIG. 24 is a flattened representation of an exemplary anvil pattern usable with the manufacturing line of FIG. 3, 8, or 16 according to another embodiment of the invention.

FIG. 24 illustrates a non-linear arrangement of the restraining weld lines 214 according to another embodiment of the invention. A sinusoidal pattern is shown that, when the elastic threads 74 and multiple web layers are bonded together, creates a distinctive gathering pattern as compared with the gathering pattern formed using the linear arrangement shown in FIG. 22. It is contemplated that the restraining weld lines 214 may form alternate arrangement patterns in other embodiments of the invention. Such other arrangement patterns may bond the elastic threads 74 and fusible web layers together in geometric or other patterns arranged in straight lines, curved lines, or otherwise arranged to create logos, pictures, other continuous and repeating patterns, or other designs on the end product.

Figure 25:
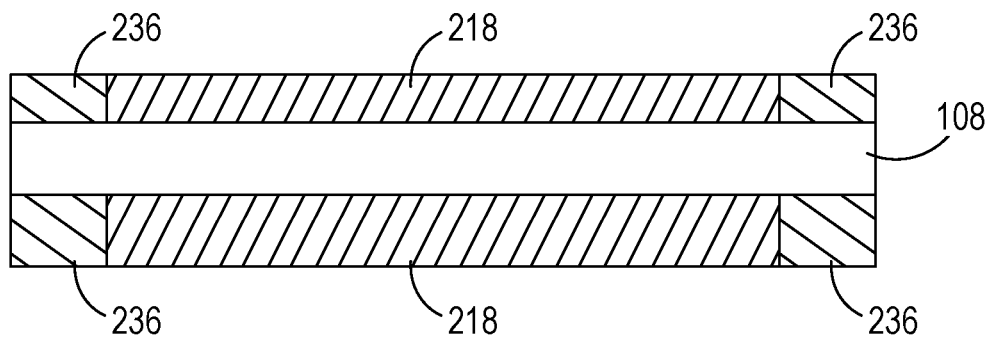
FIG. 25 is a flattened representation of an exemplary anvil pattern showing restraining bond zones and/or lamination bond zones usable with the manufacturing line of FIG. 3, 8, or 16 according to an embodiment of the invention.

FIG. 25 is a schematic diagram showing a simplified flattened representation of an exemplary anvil pattern that illustrates the locations of restraining bond zones and/or lamination bond zones usable with the manufacturing line of FIG. 3 according to an embodiment of the invention. Rotary anvil 108 schematically shows restraining region 218 between lamination regions 236. The discrete projections within regions 218 and 236 have been omitted for clarity purposes. While a flattened illustration is shown, it is understood that in a rotary or cylindrical state, the lamination regions 236 would be adjacent to one another and may comprise a continuous lamination region. The restraining and lamination regions 218, 236 adjacent a first side edge of the rotary anvil rotary anvil 108 may correspond with a cuff region while the restraining and lamination regions 218, 236 on the opposing side edge may correspond with a leg region. The weld lines in restraining regions 218 include restraining weld lines 214 for creating restrained elastics for forming an elasticized region. The weld lines in lamination portion 236 include lamination weld lines 238 for creating unrestrained elastics for forming a non-elasticized region. In alternate embodiments of the invention, the anvil pattern illustrated in FIG. 25 and in FIGS. 26-28 may be created by appropriate designs of the separate anvils of the bonding apparatuses 152 and 174.

Figure 26:
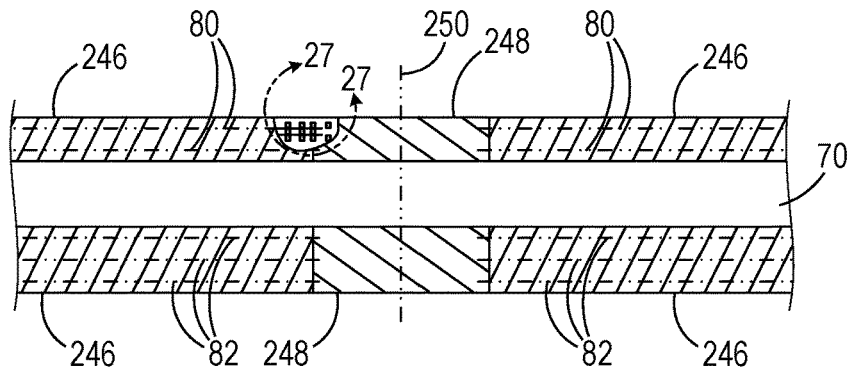
FIG. 26 illustrates an exemplary elasticized leg and leg cuff web assembly producible using the rotary anvil of FIG. 25.

FIG. 26 illustrates an exemplary elasticized leg and leg cuff web assembly 70 producible using the rotary anvil 108 of FIG. 25. In the portion of the running elasticized leg and leg cuff web assembly 70 shown, a plurality of elasticized regions 246 is created via the restraining regions 218 of FIG. 25. A plurality of non-elasticized regions 248 is created by the lamination portions 236 creating lamination bonds and later breaking or deactivating the elastic strands in the lamination region (for example, in an area along a separation line 250) using methods known in the art. When broken, the ends of the elastic strands contract back toward their respective elasticized regions 246. Further, cutting or separating the elasticized leg and leg cuff web assembly 70 along the separation line 250 discretizes the web into individual leg cuff segments having elasticized and non-elasticized regions 246, 248 available for attachment into an assembly with an absorbent core and other elements to form a disposable product such as a diaper or light incontinence product.

Figure 27:
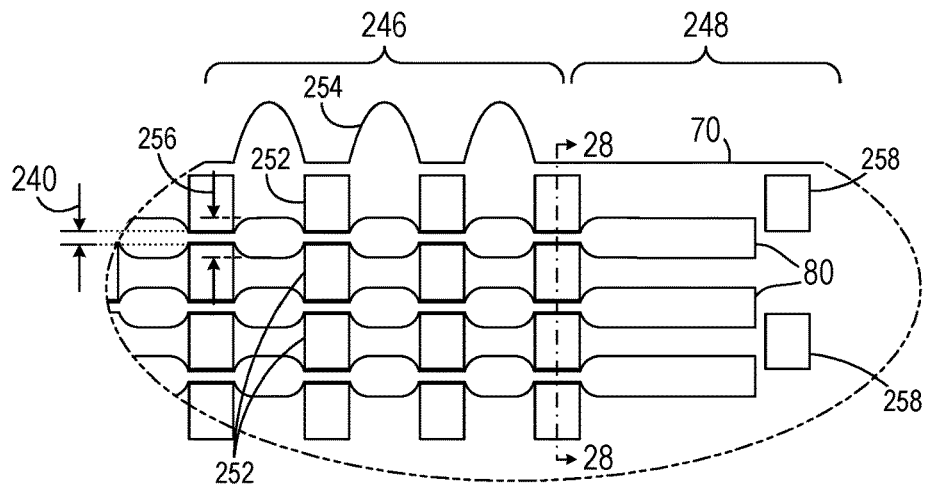
FIG. 27 is a detailed view taken along line 27-27 of FIG. 26.

FIG. 27 illustrates a detailed view of a cutaway portion of the elasticized leg and leg cuff web assembly 70 illustrated in FIG. 26. A plurality of restraining bonds 252 formed by restraining projections 226, 228 (illustrated in FIG. 23) trap or restrain the elastic thread 80 positioned between adjacent bonds 252. Bonds 252 are formed when the clastic thread 80 is in a stretched or elongated state. Further, the first web layer 72, which does not exhibit elastic properties, is in a smooth or flat state when the clastic threads 80 are stretched therealong. The separation distance 232 of the adjacent restraining projections 226 and/or 228 is sufficient to allow the stretched elastic thread 80 to be positioned between the restraining projections or the contact surfaces 242 of the restraining projections during the ultrasonic bonding that forms restraining bonds 252. The separation distance is preferably greater than the width of the stretched elastic thread but may be equal to or less than the width of the clastic thread according to embodiments of the invention.

The restraining bonds 252 fix the elastic thread 80 in position with respect to the bonded web layers affected by the restraining bonds 252. Accordingly, when the tensioned elastic thread 80 is allowed to return toward its un-tensioned or un-stretched state, the elastic thread 80 gathers the bonded web layers and causes folds 254 in the elasticized web. The un-tensioned portions of the elastic thread 80 between adjacent lines of restraining bonds 252 have a width or diameter 256 wider than the width 232 between adjacent restraining bonds 252.

As further illustrated in FIG. 27, a plurality of lamination bonds 258 of the non-elasticized region 248 formed by lamination projections 234 (illustrated in FIG. 23) bond affected web layers together (e.g., first web layer 72 with second web layer 120) without trapping or restraining the clastic thread 80 between adjacent bonds 258. The separation distance 240 of the adjacent restraining projections 234 is sufficient to allow the un-stretched clastic thread 80 to freely move with respect to the bonds 258. That is, the separation distance 240 is larger than the diameter 256 of an un-tensioned elastic thread 80. When the elastic threads 80 are cut or broken, they are free to contract toward their un-stretched state and to withdraw from a position between adjacent bonds 258 separated in the longitudinal direction 224. Bonds 258 thus do not restrain the elastic threads 80 in a manner resulting in an elastic gathering of the web layer.

Figure 28A:
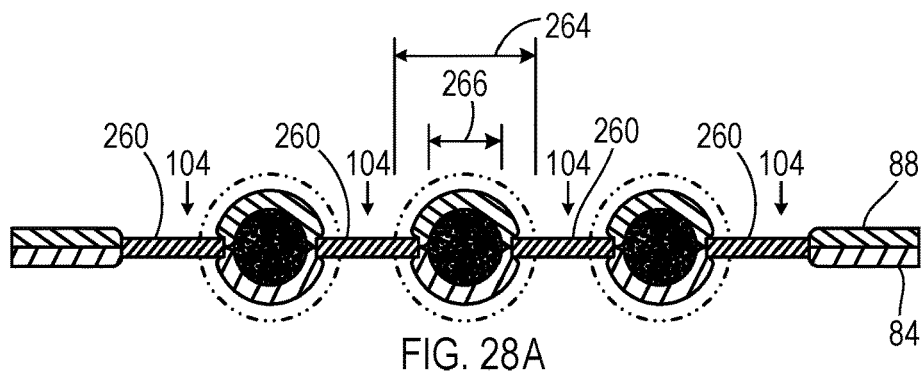
FIGS. 28A and 28B are cross-sectional views taken along line 28-28 of FIG. 27.
Figure 28B:
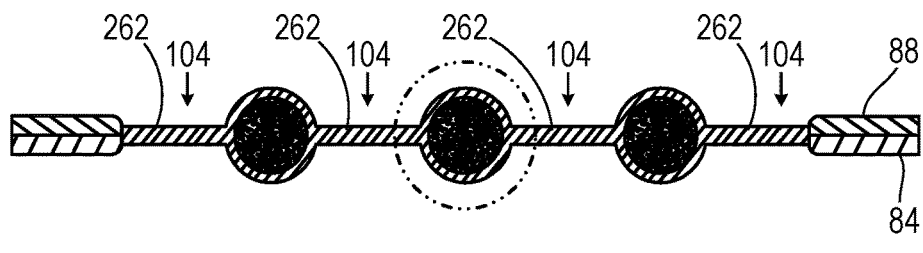

Depending on the operating parameters of the ultrasonic bonding apparatus 106 and/or the geometry and configuration of the notches and projections on the anvil 108 and/or horn 110, the resulting pair of adjacent bonds 252 either may be formed as discrete, discontinuous bonds 260, as shown in FIG. 28A that fuses the facing web layers 84, 88 together at bond sites 104 or, as shown in FIG. 28B, as a continuous fusion bond 262 and fuses one or both of the facing web layers 84, 88 together at bond sites 104. As illustrated in FIG. 28A, the un-tensioned diameter 264 is greater than the tensioned diameter 266 for the restraining bonds 252.

Figure 29:
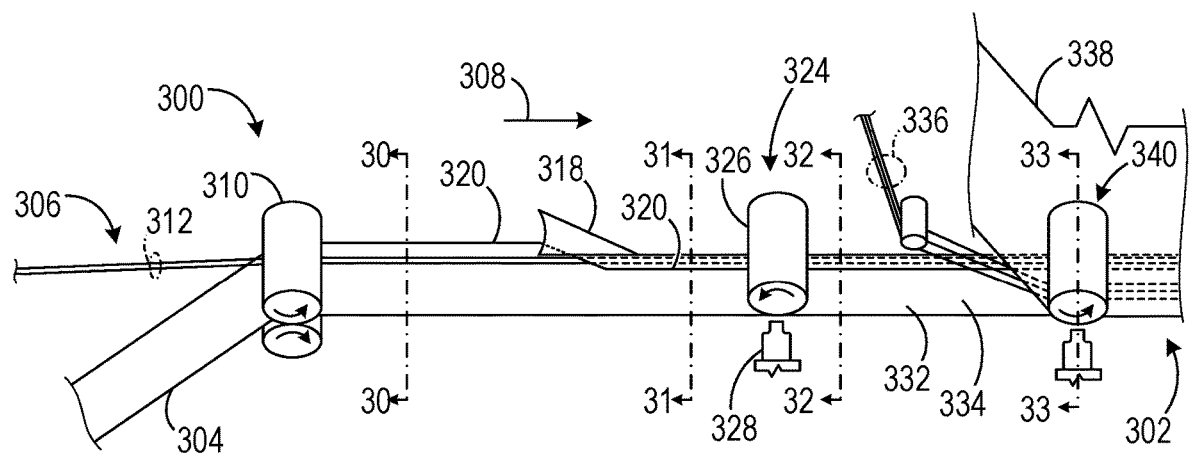
FIG. 29 is a schematic view of a portion of a manufacturing line for forming an elasticized leg and leg cuff web assembly according to another embodiment of the invention.

Referring now to FIG. 29, a portion of an exemplary manufacturing line 300 for producing an elasticized leg and leg cuff web assembly 302 is illustrated according to one embodiment of the invention. As shown, a first web layer 304 and a plurality of elastic threads or strands 306 are fed in the machine direction 308 by a roller assembly 310, which may include one or more rollers. In the illustrated embodiment, clastic threads 306 includes a group of cuff elastic threads 312. Alternative embodiments may include a single elastic thread 306. The elastic threads 306 travel in the machine direction 308 under tension from a creel assembly (not shown) or similar device. Elastic threads 306 may have any of the shapes and compositions described above with respect to elastic threads 74 and may be provided in the form of an individual elastomeric strand or be a manufactured multifilament product that includes many individual elastomeric filaments joined together, such as by a dry-spinning manufacturing process, to form a single, coalesced elastic thread 306.

Figure 30:
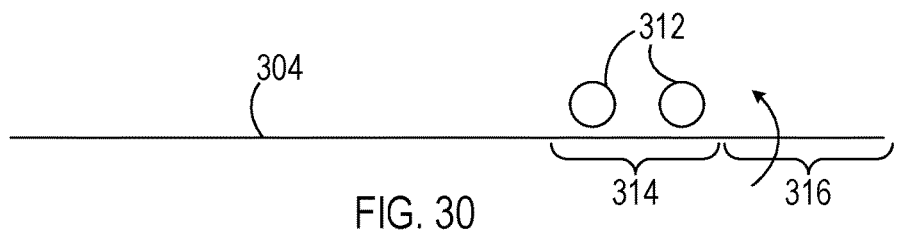
FIG. 30 is a cross-sectional view taken along line 30-30 of FIGS. 29 and 34.

Referring to FIG. 30, a cross-sectional view taken along line 30-30 of FIG. 29 is illustrated. First web layer 304 includes a cuff elastic portion 314 configured to receive the cuff clastic threads 312. In addition, first web layer 304 includes a cuff foldover portion 316 configured to be folded over at least the cuff elastic threads 312 and the cuff elastic portion 314.

Referring back to FIG. 29, first web layer 304 and elastic threads 306 travel downstream to a folding assembly 318 having a plow folder or other known folding apparatus. Folding assembly 318 is configured to fold over the cuff foldover portion 316 of first web layer 304 so as to overlap at least the cuff elastic threads 312. During folding, a cuff edge 320 of first web layer 304 is moved away from being an outside edge of the first web layer 304 on the cuff clastic side of the first web layer 304.

Figure 31:
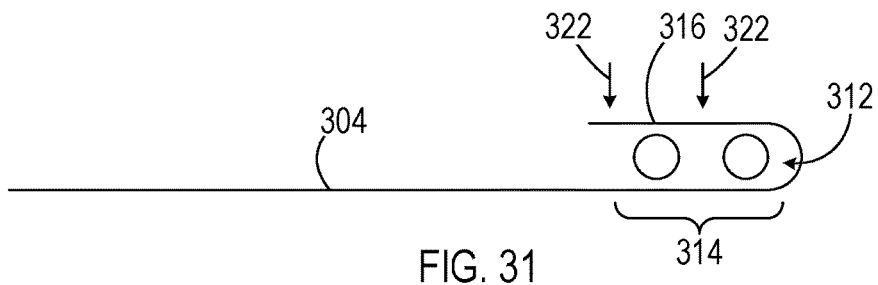
FIG. 31 is a cross-sectional view taken along line 31-31 of FIGS. 29 and 34.

As illustrated in the cross-sectional view of FIG. 31 taken along line 31-31 of FIG. 29, foldover portion 316 overlaps the cuff elastic portion 314 after the folding. A plurality of cuff bonding sites 322 are available for bonding the cuff elastic portion 314 to the foldover portion 316 as described below.

Referring back to FIG. 29, downstream of the folding assembly 318, a bonding apparatus 324 is positioned to receive the assembly of the first web layer 304 with folded portions about the elastic threads 306 to bond the cuff elastic portion 314 to the foldover portion 316 at the bonding sites 322. Bonding apparatus 324 may be any known ultrasonic welding system in alternative embodiments, including, as non-limiting examples, a rotary ultrasonic welding system or a blade ultrasonic welding system. In the illustrated embodiment, bonding apparatus 324 includes a rotary anvil 326 and an ultrasonic fixed blade horn 328, also known as a sonotrode, which cooperate with each other to bond (i.e., fuse) the cuff elastic portion 314 to the foldover portion 316. Alternative embodiments may include multiple fixed blade horns or one or more rotary horns. As illustrated in the cross-section view of FIG. 32 taken along line 32-32 of FIG. 29, during the bonding process, the elastic threads 312 may be secured in position relative to the first web layer 304 by cuff bonds 330 to create elasticized regions of the elasticized leg and leg cuff web assembly 302 or may be unsecured by the bonds 330 so as to freely move independently of the first web layer 304 in non-elasticized regions of the elasticized leg and leg cuff web assembly 302.

The ultrasonic emission of energy from bonding apparatus 324 is concentrated at specific bond points where frictional heat fuses the layers of web together without the need for consumable adhesives. While bonding apparatus 324 is described herein as an ultrasonic bonding assembly that ultrasonically fuses layers of web together, it is contemplated that the techniques described herein may be extended to any other known welding or bonding techniques that fuse together two or more material layers without the use of adhesive, including ultrasonic, thermal, or pressure bonding techniques and various other forms of welding known in the industry.

As shown in FIG. 29, after the bonding by the bonding apparatus 324, a leg elastic portion 332 of an elasticized cuff web 334 produced so far is left unprocessed by the bonding apparatus 324 for further processing downstream. One or more leg elastic threads 336 and a second web layer 338 such as a topsheet are brought into a position adjacent to the leg elastic portion 332, and a second bonding apparatus 340 bonds the second web layer 338 to the leg elastic portion 332 of the elasticized cuff web 334 with the leg elastic threads 336 positioned therebetween. Bonding apparatus 340 may be similar to the bonding apparatus 324 described herein.

Figure 33A:
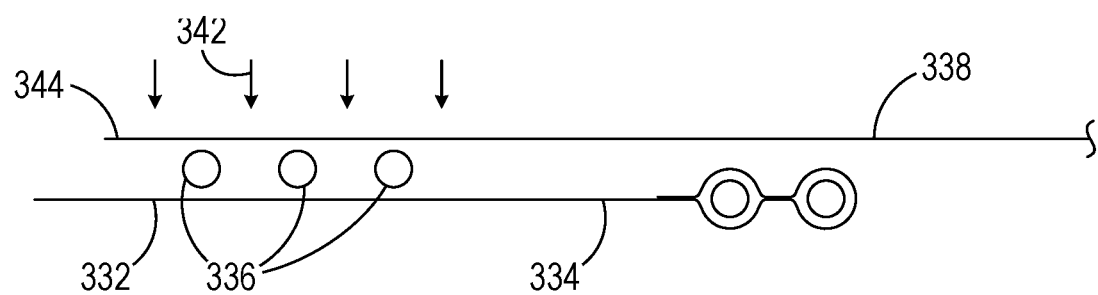
FIGS. 33A and 33B are cross-sectional views taken along line 33-33 of FIG. 29.

As illustrated in FIG. 33A taken along line 33-33 of FIG. 29, positioning the leg elastic threads 336 and the second web layer 338 adjacently to the elasticized cuff web 334 presents leg bonding sites 342 for bonding a leg elastic portion 344 of the second web layer 338 to the leg elastic portion 332 of the elasticized cuff web 334.

Figure 33B:
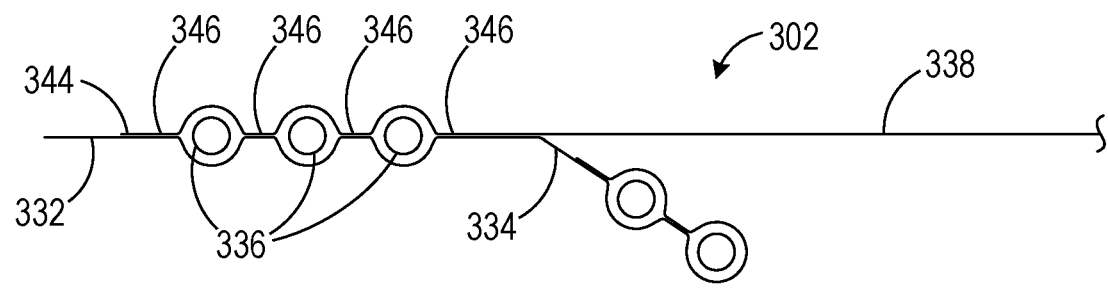

FIG. 33B of line 33-33 of FIG. 29 illustrates the elasticized leg and leg cuff web assembly 302 including the elasticized cuff web 334 bonded to the second web layer 338 via the bonding apparatus 340. During the bonding process, portions of the elastic threads 336 may be secured in position relative to the first and second web layers 304, 338 by leg bonds 346 to create elasticized regions of the elasticized leg and leg cuff web assembly 302 or may be unsecured by the bonds so as to freely move independently of the first and second web layers 304, 338 in non-elasticized regions of the elasticized leg and leg cuff web assembly 302.

FIG. 34 illustrates a portion of an exemplary manufacturing line 348 for producing an elasticized leg and leg cuff web assembly 350 according to another embodiment of the invention. A first portion of manufacturing line 348 is similar to that described in FIGS. 29-32, and similar portions that are numbered identically and not described or referenced below are as described above and, for simplicity, will not be repeated.

As shown in FIG. 34, after the bonding by the bonding apparatus 324, the leg elastic threads 336 and the second web layer 338 are brought into a position adjacent to the elasticized cuff web 334 via a roller assembly 352. Referring to FIGS. 34 and 35, a leg edge 354 of second web layer 338 is folded via a folding assembly 356 so as to wrap a leg foldover portion 358 about a distal end 360 of the elasticized cuff web 334. The presentation of the leg elastic thread 336 and the second web layer 338 adjacently to the elasticized cuff web 334 presents bond sites 362 for bonding the second web layer 338 to the elasticized cuff web 334 to create the elasticized leg and leg cuff web assembly 350.

As illustrated in FIG. 34, after the folding assembly 356, bonding apparatus 340 bonds the second web layer 338 to the elasticized cuff web 334 to create the elasticized leg and leg cuff web assembly 350. FIG. 36 taken along line 36-36 of FIG. 34 illustrates the elasticized cuff web 334 bonded to the second web layer 338 via the bonding apparatus 340. During the bonding process, portions of the elastic threads 336 may be secured in position relative to the first and second web layers 304, 338 by leg bonds 364 by the bonds to create elasticized regions of the elasticized leg and leg cuff web assembly 350 or may be unsecured by the bonds so as to freely move independently of the first and second web layers 304, 338 in non-elasticized regions of the elasticized leg and leg cuff web assembly 350.

Figure 37:
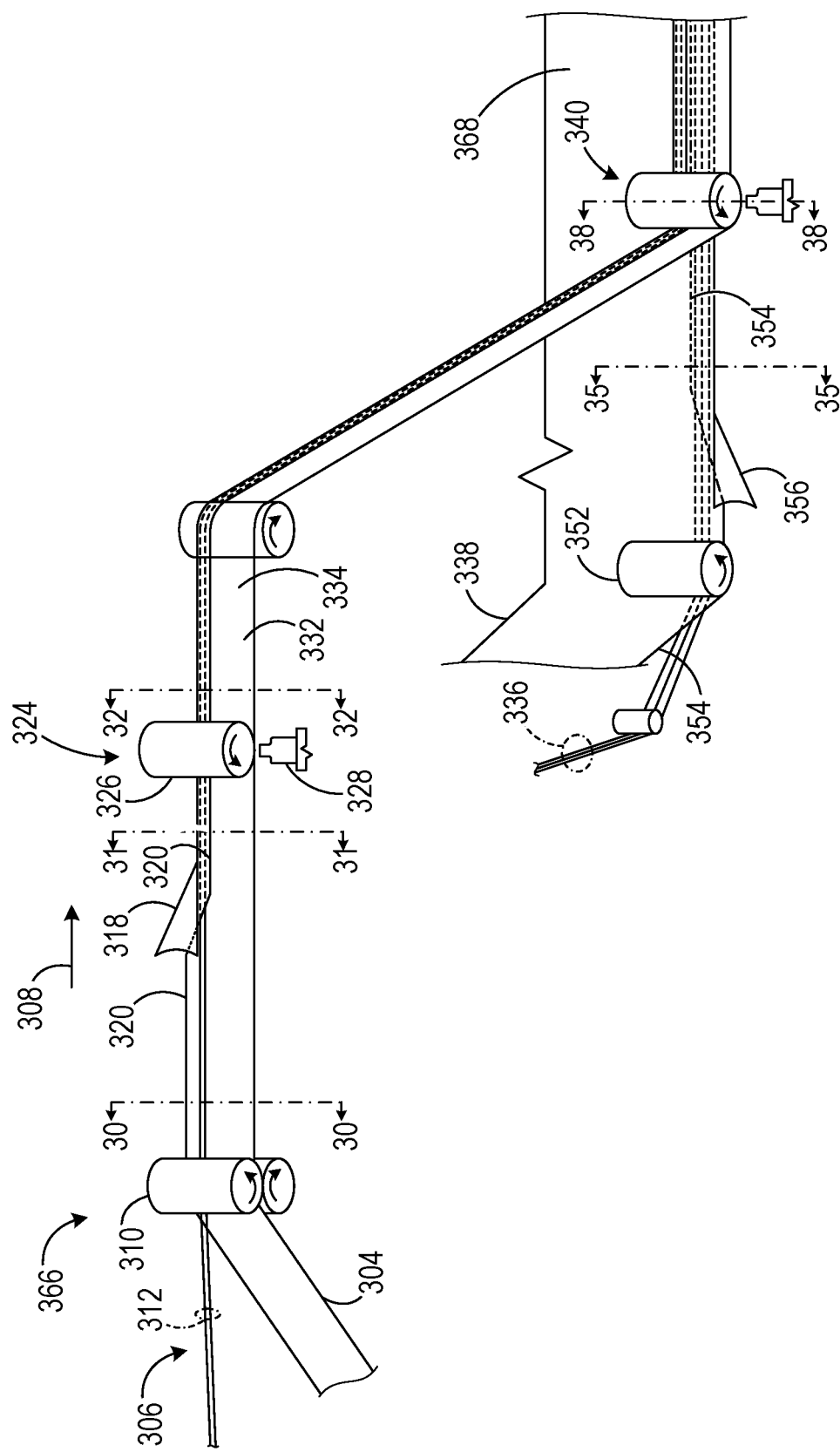
FIG. 37 is a schematic view of a portion of a manufacturing line for forming an elasticized leg and leg cuff web assembly according to another embodiment of the invention.

FIG. 37 illustrates a portion of an exemplary manufacturing line 366 for producing an elasticized leg and leg cuff web assembly 368 according to another embodiment of the invention. A first portion of manufacturing line 366 is similar to that described in FIGS. 29-32 and 34-35, and similar portions that are numbered identically and not described or referenced below are as described above and, for simplicity, will not be repeated.

Figure 38A:
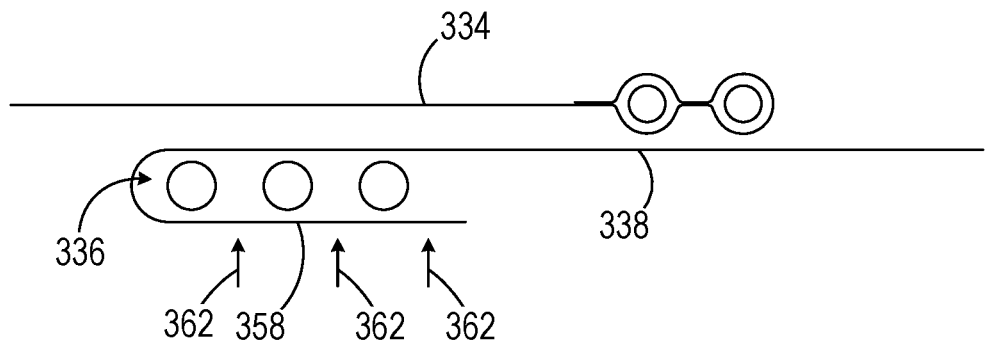
FIGS. 38A and 38B are cross-sectional views taken along line 38-38 of FIG. 37.

Downstream of bonding apparatus 324, the elasticized cuff web 334 is joined together with the second web layer 338 after the leg edge 354 has been folded around the leg elastic threads 336. The joining occurs via the bonding apparatus 340. As illustrated in the cross-section view of FIG. 38A taken along line 38-38 of FIG. 37, the bond sites 362 are presented for bonding the leg elastic portion 332 of the elasticized cuff web 334 to the second web layer 338.

Figure 38B:
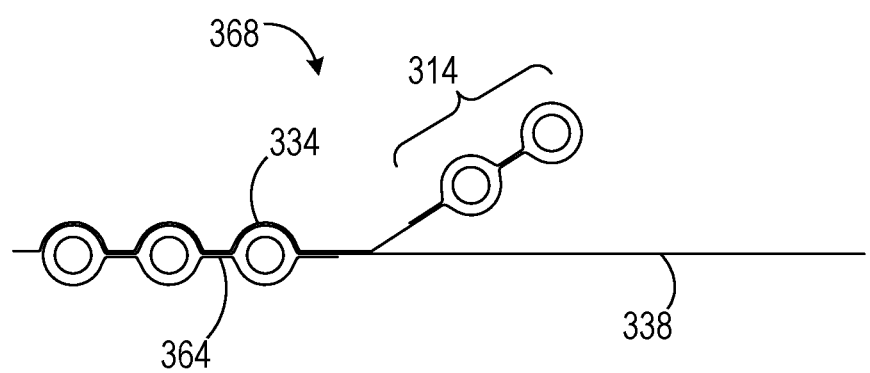

FIG. 38B taken along line 38-38 of FIG. 37 illustrates the elasticized cuff web 334 bonded to the second web layer 338 via the bonding apparatus 340. During the bonding process, portions of the elastic threads 336 may be secured in position relative to the first and second web layers 304, 338 by leg bonds 364 to create elasticized regions of the elasticized leg and leg cuff web assembly 368 or may be unsecured by the bonds so as to freely move independently of the first and second web layers 304, 338 in non-elasticized regions of the elasticized leg and leg cuff web assembly 368.

Figure 39:
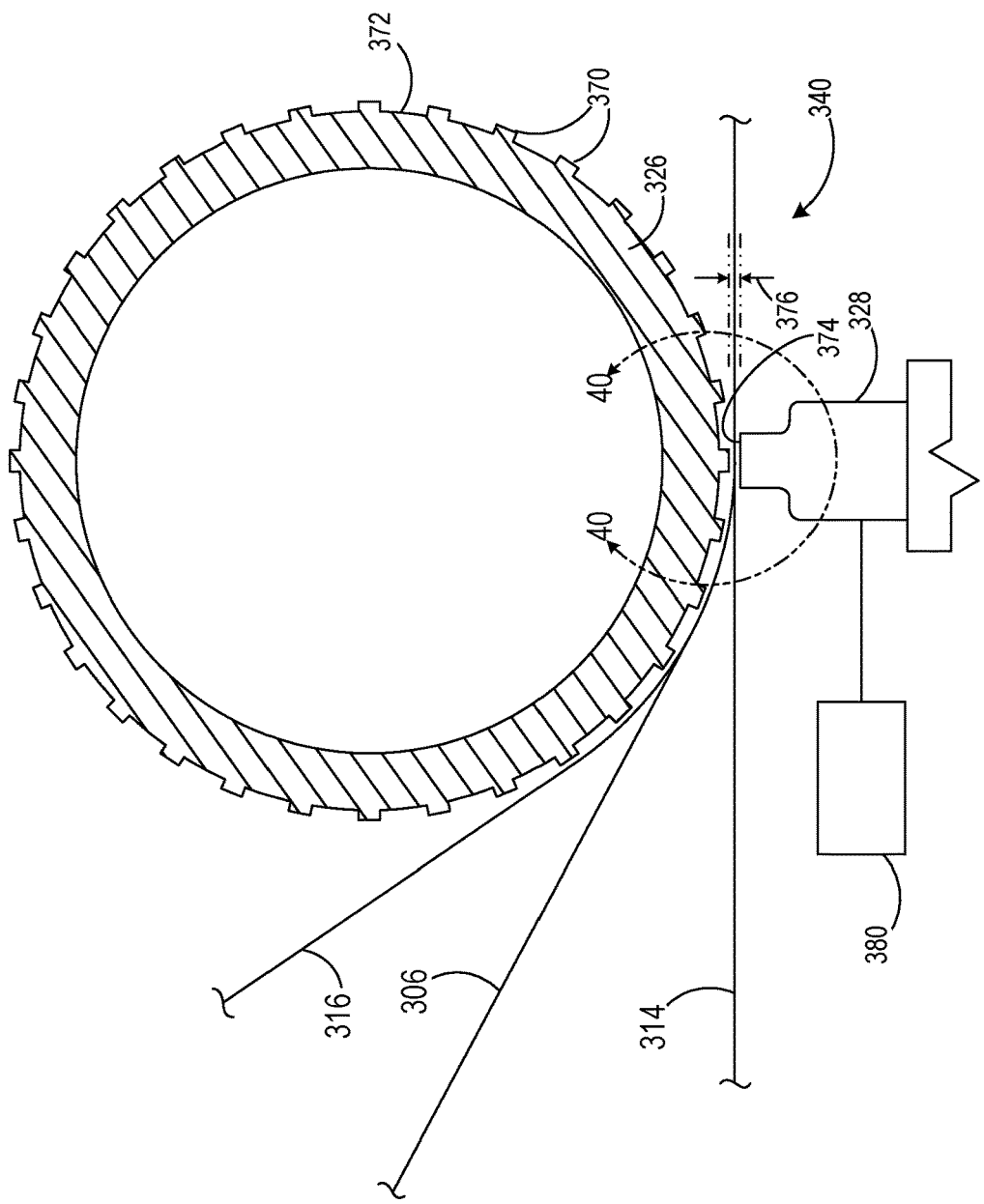
FIG. 39 is a schematic cross-sectional view of a bonding apparatus that is usable with the manufacturing line of FIG. 29, 34, or 37 according to one embodiment of the invention.

Referring now to FIG. 39, anvil 326 is illustrated according to one embodiment of the invention. As shown, the anvil 326 includes an arrangement of discrete projections 370 that extend outward from the anvil face 372. These projections 370 are constructed to (A) fuse the two sheets or sheet layers (e.g., the cuff elastic portion 314 to the cuff foldover portion 316, the leg elastic portion 332 to the second web layer 338, etc.) together and (B) restrain or hold the elastic threads 306, 336 in position relative to the layers in the manufactured elastic composite structure (e.g., the elasticized leg and leg cuff web assembly 302). As described in more detail below, restraining projections 370 are designed so that an elastic thread 306 that passes between two adjacent restraining projections 370 on the face 372 of anvil 326 is restrained in position relative to the web layers 314, 316 by frictional resistance that prevents the elastic thread 306 from sliding through the pair of resulting bonds.

The particular size, shape, and general arrangement of restraining projections 370 as well as the total number of projections 370 illustrated in FIG. 39 are intended to depict a representative and non-limiting example of an overall pattern of projections 370 on anvil 326. Alternative embodiments may include any number of projections 370 arranged in any number of alternative configurations to achieve a desired pattern of bonds on the end product. The respective working surfaces of restraining projections 370 may be configured to form bonds of similar size and shape, or bonds of different size and/or shape in alternative embodiments. As non-limiting examples, respective land surfaces of restraining projections 370 may be circular, rectangular, crescent shaped, or have irregular shapes that may be selected to form a desired overall pattern on the end product. The resulting pattern of bonds will include one or more restrained zones, which fix or anchor one or more elastic threads 306 under tension in position relative to the fused sheets.

In a preferred embodiment, the restraining projections 370 are formed on anvil 326 using a machining process that removes bulk material from the anvil 326 to create the desired raised pattern of projections 370 relative to the face 372 of the anvil 326. Alternatively, restraining projections 370 may be provided on one or more inserts that are mechanically coupled to the face 372 of the anvil 326.

Still referring to FIG. 39, the working surface 374 of the horn 328 has a smooth or substantially smooth surface contour in one non-limiting embodiment. Alternatively, working surface 374 may include an arrangement of projections 370 and/or grooves that mate or align with the pattern of projections 370 on the anvil 326 to further facilitate fusing the web layers 314, 316 and securing the elastic threads 306 in position relative thereto.

Figure 40:
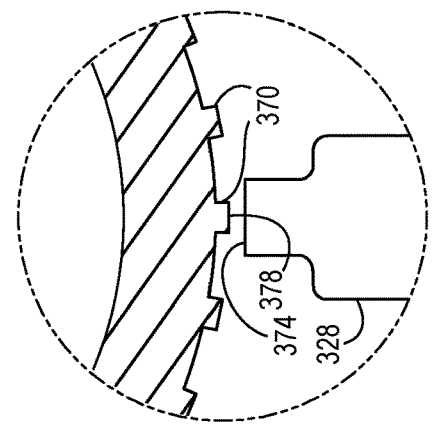
FIG. 40 is a detailed view of a portion of the bonding apparatus of FIG. 39 illustrating the horn aligned with a projection on the rotary anvil, according to one embodiment of the invention.

During the manufacturing process, the web layers 314, 316 are positioned between the face 372 of the anvil 326 and the working surface 374 of the horn 328 as shown in FIG. 39. Elastic threads 306 are positioned between the web layers 314, 316 in a tensioned state. As generally shown in FIG. 39 and in further detail in FIG. 40, the position of horn 328 is controlled to maintain a nip gap 376 between the working surface 374 of horn 328 and the land surfaces 378 of the restraining projections 370. The size of the nip gap 376 is determined based on parameters of the manufacturing process to facilitate bonding between the web layers 314, 316. Bonding apparatus 324 may include any known positioning means 380 that exerts a force on at least one of the horn 328 and anvil 326 to maintain a desired nip gap 376 between the horn 328 and anvil 326. Positioning means 380 may be an air pressure assembly (not shown) or a mechanical camshaft (not shown) as non-limiting examples.

Restraining projections 370 may have a planar working surface, planar side surfaces, or some mixture of curved and straight working and side surfaces in alternative embodiments. In the embodiment illustrated in FIG. 40, the land surface 378 of restraining projection 370 has planar working and side surfaces. In alternative embodiments where the land surface 378 has an arced or curved surface profile, this curved profile permits the web layers 314, 316 to slip relative to the face 372 of the anvil 326 during the bonding process and thus allows the velocity at which the combined assembly of the tensioned elastic strands 306 and web layers 314, 316 is advanced toward the bonding apparatus 324 to be increased or decreased relative to the rotational velocity of the anvil 326. When the combined web/thread assembly is advanced at a velocity greater than the velocity of the anvil 326, the resulting bonds are spaced apart by a distance greater than the radial spacing between adjacent projections 370 on the anvil face 372. Similarly, slowing the feed rate of the combined web/thread assembly relative to the velocity of the anvil 326 will result in bonds that are spaced apart by a distance less than the radial spacing between adjacent projections 370 on the anvil face 372. The velocity mismatch or differential between web speed and anvil velocity can be controlled to accommodate size changes in the end product. As a result, the bonding of an elastic composite for one size diaper may be carried out with little or no slip, while the bonding of an elastic composite for a larger or smaller diaper may be carried out with a larger amount of slip. A manufacturing line of FIG. 29, 34, or 37 outfitted with an anvil that includes projections 370 with curved surface profiles thus provides for dynamic size changing without having to change the tooling set-up of the manufacturing line, as the same anvil can be used to manufacture multiple sizes of elastic composite structures for use in different sized products.

FIG. 41 is a flattened representation of the circumferential face 372 of anvil 326 according to an embodiment where anvil 326 includes a pattern of projections 382 that form restrained zones. The pattern of projections 382 includes multiple restraining weld lines 384 that are spaced apart from one another along the circumferential axis 386 of the anvil face 372. The restraining weld lines 384 define one or more restraining regions 388 of the projection pattern 382. As with restraining projections 370 above, in a preferred embodiment, the restraining weld lines 384 are formed on anvil 326 using a machining process that removes bulk material from the anvil 326 to create the desired raised pattern of restraining weld lines 384 relative to the face 372 of the anvil 326. Alternatively, restraining weld lines 384 may be provided on one or more inserts that are mechanically coupled to the face 372 of the anvil 326.

FIG. 41 illustrates restraining weld lines 384 having separate welding line portions 390, 392 on opposite sides of the face 372 along the longitudinal direction 394 of the rotary anvil 326. The longitudinal direction 394 generally extends in the cross-machine direction. The spacing between adjacent restraining weld lines 384 as well as the length and placement of each restraining weld line 384 along the longitudinal direction 394 may be subject to the design of the bond pattern desired in the finished product.

As shown more specifically in the detailed view provided in FIG. 42, each weld line 384 contains a pattern of discrete projections 396, 398 that extend outward away from the face 372 of the anvil 326. The projections 396, 398 are spaced apart from one another, by a notch 400 that is defined by the width of a gap 402 positioned between a given pair of adjacent projections 396, 398. The width or size of the gap 402 may restrain one or more elastic threads 306 between adjacent bonds formed by projections 396, 398 such that the elastic thread(s) 306 is held tightly by and between the adjacent bonds. In this manner, for example, the adjacent bonds constrain the elastic thread(s) 306 such that the elastic thread(s) 306 is restrained between the adjacent bonds to create an elasticized region absent the use of adhesives. Elasticized regions are formed by the projections in the restraining region section 388 of the rotary anvil 326.

Anvil 326 may in addition or alternatively include one or more projections that are referred to herein as lamination or non-restraining projections 404. As illustrated in FIG. 41, a plurality of lamination projections 404 are shown in one or more lamination portions 406 of the rotary anvil 326 in lamination weld lines 408. Lamination projections 404, similar to the restraining or restraining projections 396, 398, fuse two web layers to one another. Lamination projections 404 differ from restraining projections 396, 398 because they do not restrain the elastic threads 306, 336 in position relative to the fused web layers due to the spacing of the gap 410 between adjacent projections 396, 398. Accordingly, a broken elastic thread 306, 336 is free to contract out of the gap between the adjacent lamination weld bonds if the length of the contraction is sufficient. Such lamination projections 404 are advantageous, for example, when laminating two web layers in areas designed for elastic deactivation in which the elastic threads 306, 336 are purposely broken in order to create a non-elastic portion of the bonded web layers. Embodiments of the invention contemplate the use or non-use of any number and placement of the lamination projections 404.

Referring to FIG. 42, it is contemplated that the contact surfaces 412 of the projections 396, 398 may have different geometries in alternative embodiments. As non-limiting examples, projections 396, 398 may be circular, rectangular, crescent shaped, or have irregular shapes that may be selected to form a desired overall pattern on the end product. In yet another embodiment, corresponding projections 396, 398 of adjacent weld lines 384 may be aligned with one another in a line parallel to the circumferential axis 386. Alternatively, projections 396, 398 of sequential weld lines 384 may be offset from one another in the cross-machine direction thereby defining a stepped or non-linear passage through the bond lines that are formed on the fused web layers.

Referring again to FIG. 41, an alternative weld line 414 is illustrated as an example to show another embodiment in which a weld line extends a majority of the width of the anvil 326 in the longitudinal direction 394. As shown, restraining weld line 414 includes both restraining projections 396 and lamination projections 404. The combination of projections 396, 404 may also be designed into any of the other weld lines 384, 408 as well. Alternatively, weld line 414 may include only one of the types of projections 396, 404 in other embodiments.

FIGS. 41 and 42 illustrate an elastic thread (such as cuff elastic thread 312) in phantom in a stretched state extending between adjacent restraining projections 396 and/or 398 of restraining weld lines 384 and between adjacent lamination projections 404 of lamination weld lines 408. The restraining bonds (illustrated in FIG. 46) formed by adjacent restraining projections 396, 398 may form separate, independent bonds spaced apart by a distance less than the diameter or width of the un-stretched elastic thread or may form a single bond across the elastic thread from one contact surface 412 to the other contact surface 412 on the other side of the elastic thread.

Figure 43:
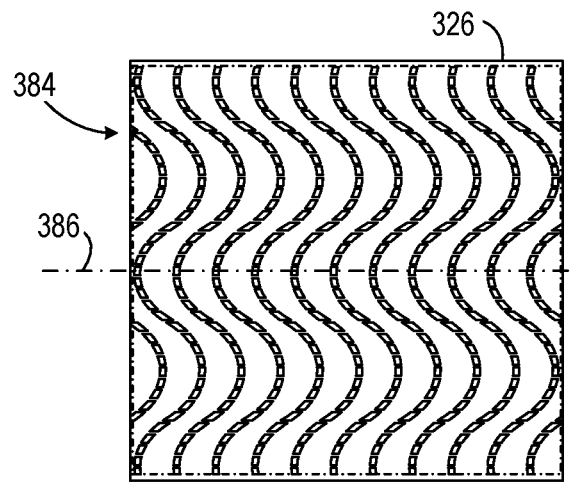
FIG. 43 is a flattened representation of an exemplary anvil pattern usable with the manufacturing line of FIG. 29, 34, or 37 according to another embodiment of the invention.

FIG. 43 illustrates a non-linear arrangement of the restraining weld lines 384 according to another embodiment of the invention. A sinusoidal pattern is shown that, when the elastic threads 306, 336 and the web layers are bonded together, creates a distinctive gathering pattern as compared with the gathering pattern formed using the linear arrangement shown in FIG. 41. It is contemplated that the restraining weld lines 384 may form alternate arrangement patterns in other embodiments of the invention. Such other arrangement patterns may bond the elastic threads 306, 336 and the web layers together in geometric or other patterns arranged in straight lines, curved lines, or otherwise arranged to create logos, pictures, other continuous and repeating patterns, or other designs on the end product.

Figure 44:
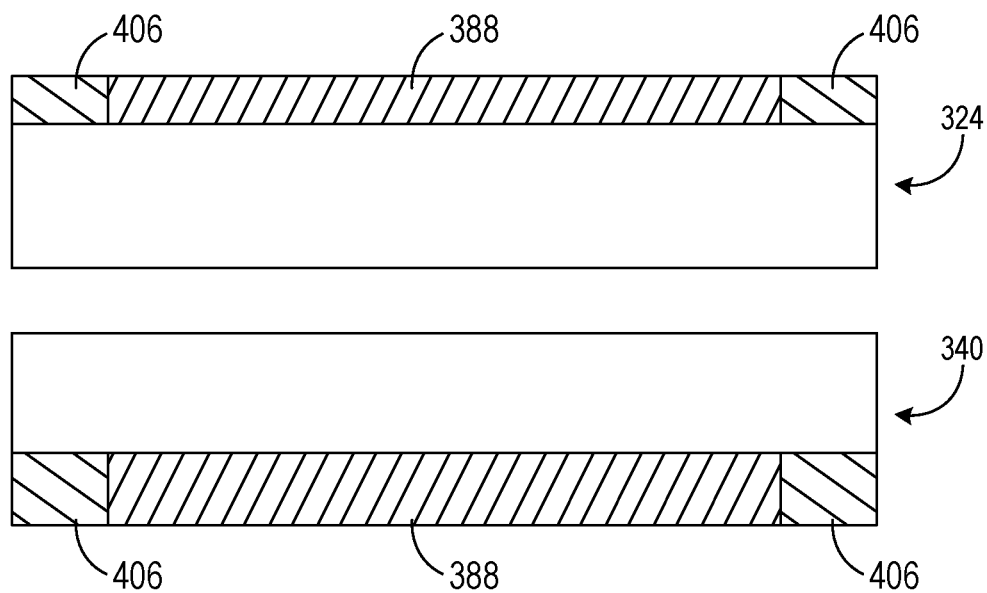
FIG. 44 is a flattened representation of an exemplary anvil pattern showing restraining bond zones and/or lamination bond zones usable with the manufacturing line of FIG. 29, 34, or 37 according to an embodiment of the invention.

FIG. 44 is a schematic diagram showing a simplified flattened representation of exemplary anvil patterns that illustrate the locations of restraining bond zones and/or lamination bond zones usable with the manufacturing line of FIG. 29, 34, or 37 according to an embodiment of the invention. Rotary anvils of bonding apparatuses 324, 340 schematically shows restraining region 388 between lamination regions 406. The discrete projections within regions 388 and 406 have been omitted for clarity purposes. While a flattened illustration is shown, it is understood that in a rotary or cylindrical state, the lamination regions 406 would be adjacent to one another and may comprise a continuous lamination region. The restraining and lamination regions 388, 406 adjacent to a first side edge of the rotary anvil of bonding apparatus 324 may correspond with a cuff region while the restraining and lamination regions 388, 406 on an opposing side edge of the rotary anvil of bonding apparatus 340 may correspond with a leg region. The weld lines in restraining regions 388 include restraining weld lines 384 for creating restrained elastics for forming an elasticized region. The weld lines in lamination portion 406 include lamination weld lines 408 for creating unrestrained elastics for forming a non-elasticized region.

Figure 45:
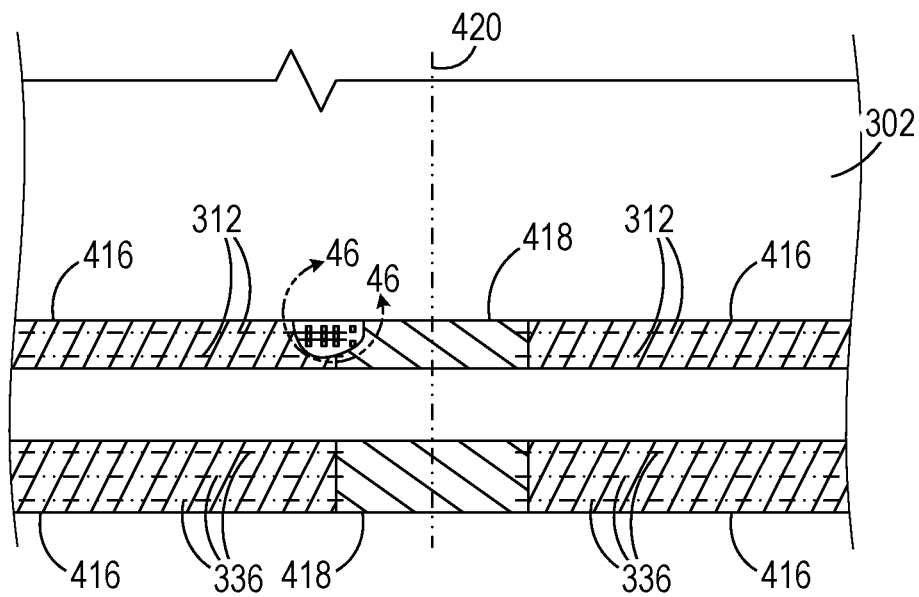
FIG. 45 illustrates an exemplary elasticized leg and leg cuff web assembly producible using the rotary anvil of FIG. 44.

FIG. 45 illustrates an exemplary portion of the elasticized leg and leg cuff web assembly 302 producible using the rotary anvil 326 of FIG. 44. In the portion of the running elasticized leg and leg cuff web assembly 302 shown, a plurality of elasticized regions 416 is created via the restraining regions 388 of FIG. 44. A plurality of non-elasticized regions 418 is created by the lamination portions 406 creating lamination bonds and later breaking or deactivating the elastic strands in the lamination region (for example, in an area along a separation line 420) using methods known in the art. When broken, the ends of the elastic strands contract back toward their respective elasticized regions 416. Further, cutting or separating the elasticized leg and leg cuff web assembly 302 along the separation line 420 discretizes the web into individual leg cuff segments having elasticized and non-elasticized regions 416, 418 available for attachment into an assembly with an absorbent core and other elements to form a disposable product such as a diaper.

Figure 46:
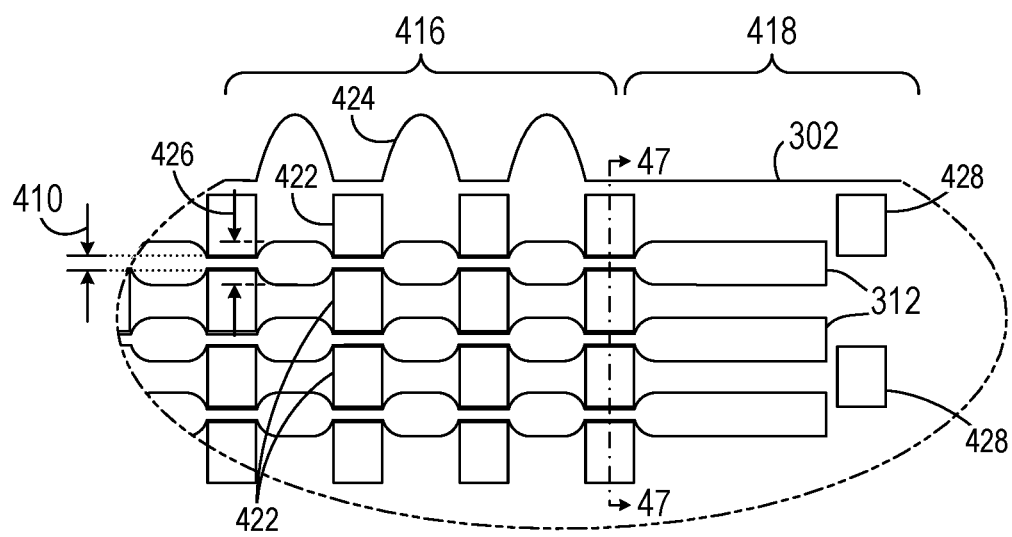
FIG. 46 is a detailed view taken along line 46-46 of FIG. 45.

FIG. 46 illustrates a detailed view of a cutaway portion of the elasticized leg and leg cuff web assembly 302 illustrated in FIG. 45. A plurality of restraining bonds 422 formed by restraining projections 396, 398 (illustrated in FIG. 42) trap or restrain the elastic thread 312 positioned between adjacent bonds 422. Bonds 422 are formed when the elastic thread 312 is in a stretched or elongated state. Further, the first web layer 304, which does not exhibit elastic properties by itself, is in a smooth or flat state when the elastic threads 312 are stretched therealong. The separation distance 402 of the adjacent restraining projections 396 and/or 398 is sufficient to allow the stretched elastic thread 312 to be positioned between the restraining projections or the contact surfaces 412 of the restraining projections during the ultrasonic bonding that forms restraining bonds 422. The separation distance is preferably greater than the width of the stretched elastic thread but may be equal to or less than the width of the elastic thread according to embodiments of the invention.

The restraining bonds 422 fix the elastic thread 312 in position with respect to the bonded web layers affected by the restraining bonds 422. Accordingly, when the tensioned elastic thread 312 is allowed to return toward its un-tensioned (or un-stretched) state, the elastic thread 312 gathers the bonded web layers and causes folds 424 in the elasticized web. The un-tensioned portions of the elastic thread 312 between adjacent lines of restraining bonds 422 have a width or diameter 426 wider than the width 402 between adjacent restraining bonds 422.

As further illustrated in FIG. 46, a plurality of lamination bonds 428 of the non-elasticized region 418 formed by lamination projections 404 (illustrated in FIG. 42) bond affected web layers together (e.g., first web layer 304 with second web layer 338) without trapping or restraining the elastic thread 312 between adjacent bonds 428. The separation distance 410 of the adjacent restraining projections 404 is sufficient to allow the un-stretched elastic thread 312 to freely move with respect to the bonds 428. That is, the separation distance 410 is larger than the diameter 426 of an un-tensioned elastic thread 312. When the elastic threads 312 are cut or broken, they are free to contract toward their un-stretched state and to withdraw from a position between adjacent bonds 428 separated in the longitudinal direction 394. Bonds 428 thus do not restrain the elastic threads 312 in a manner resulting in an elastic gathering of the web layer.

Depending on the operating parameters of the ultrasonic bonding apparatus 324 and/or the geometry and configuration of the notches and projections on the anvil 326 and/or horn 328, the resulting pair of adjacent bonds 422 either may be formed as discrete, discontinuous bonds 430, as shown in FIG. 47A that fuses the facing web layers 304, 338 together at bond sites 322 or, as shown in FIG. 47B, as a continuous fusion bond 432 and fuses one or both of the facing web layers 304, 338 together at bond sites 322. As illustrated in FIG. 47A, the un-tensioned diameter 434 is greater than the tensioned diameter 436 for the restraining bonds 422.

Figure 32:
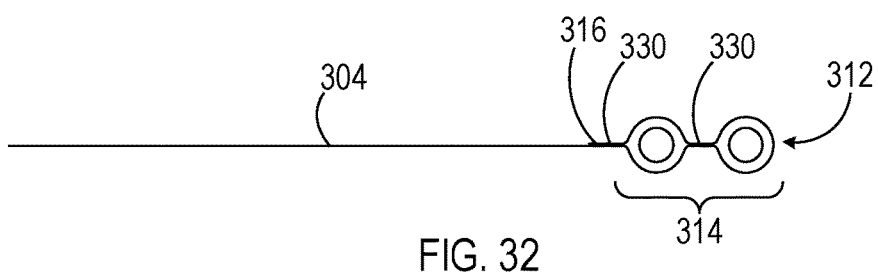
FIG. 32 is a cross-sectional view taken along line 32-32 of FIGS. 29 and 34.

FIG. 48 is a schematic diagram showing a flattened representation of exemplary anvil patterns showing restraining bond zones and/or lamination bond zones usable with the manufacturing lines of FIG. 29, 34, or 37 according to an exemplary and non-limiting embodiment of the invention. Similar to that illustrated in FIG. 44, the anvil of bonding apparatus 324 is designed to contain restraining region 388 between lamination regions 406. The discrete projections of each region 388, 406 are omitted from FIG. 48 for clarity purposes. The restraining and lamination regions 388, 406 on the illustrated side of the rotary anvil 326 may correspond with a cuff region as shown in FIG. 32. The joining of the elasticized cuff web 334 to the second web layer 338 as illustrated in FIGS. 29, 33, 34, and 36-38 may be accomplished via a bonding pattern according to the pattern illustrated for the anvil of bonding apparatus 340 shown in FIG. 48. A restraining zone 438 together with a lamination region 440 on the side of the anvil of bonding apparatus 340 opposite that of the regions 388, 406 for the anvil of bonding apparatus 324 creates bonds for the leg elastic threads 336 as described above. In addition, lamination regions 440 include lamination bonds extending toward the cuff elastic side as shown to secure the ends of the elasticized assembly across a width thereof beyond the cuff elastics to the second web layer 338. In this manner, a portion of the elasticized assembly 302 remains free to move with respect to the second web layer 338 (as illustrated in FIGS. 33, 36, and 38) while the end portions are fixed to the second web layer 338. The patterned areas of the anvil of bonding apparatus 340 are illustrated in phantom on the anvil of bonding apparatus 324 to show the overlap of the lamination regions 406, 440.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description but is only limited by the scope of the appended claims.

What is claimed is:

1. An apparatus for forming an elastic composite structure, the apparatus comprising:
   a first plurality of rollers configured to guide a first portion of a combined web assembly in a machine direction, the first portion of the combined web assembly comprising:
     a first web layer comprising a cuff elastic portion and a cuff foldover portion; and
     a plurality of cuff elastics positioned between the cuff elastic portion and the cuff foldover portion;
   a first bonding apparatus having a first horn and anvil configured to bond the cuff elastic portion to the cuff foldover portion absent adhesive via a plurality of cuff bonds that restrain the plurality of cuff elastics relative to the first web layer;
   a second plurality of rollers configured to guide a second portion of the combined web assembly in a machine direction, the second portion of the combined web assembly comprising:
     a first leg elastic portion of the first web layer;
     a second web layer comprising a second leg elastic portion; and
     a plurality of leg elastics positioned between the leg elastic portion of the first web layer and the leg elastic portion of the second web layer;
   a second bonding apparatus having a second horn and anvil configured to bond the leg elastic portion of the first web layer,
   wherein the leg elastic portion of the second web layer is absent adhesive via a plurality of leg bonds that restrain the plurality of leg elastics relative to the first and second web layers; and
   a folding apparatus configured to fold the cuff foldover portion over the cuff elastic portion.

2. The apparatus of claim 1, wherein the anvil of the first bonding apparatus comprises an arrangement of discrete projections that bond the cuff elastic portion to the cuff foldover portion such that each cuff elastic of the plurality of cuff elastics is positioned between a respective pair of the plurality of cuff bonds; and
   wherein the anvil of the second bonding apparatus comprises an arrangement of discrete projections that bond the leg elastic portion of the first web layer and the leg elastic portion of the second web layer such that each leg elastic of the plurality of leg elastics is positioned between a respective pair of the plurality of leg bonds.

3. The apparatus of claim 2, wherein a distance between the respective pair of the plurality of leg bonds comprises a restraining distance spaced apart less than a diameter of a leg elastic of the plurality of leg elastics in an un-tensioned state; and
   wherein a distance between the respective pair of the plurality of cuff bonds comprises a restraining distance spaced apart less than a diameter of a cuff elastic of the plurality of cuff elastics in an un-tensioned state.

4. The apparatus of claim 1 wherein the folding apparatus is configured to fold a portion of the first leg elastic portion of the first web layer over a portion of the second leg elastic portion of the second web layer.

5. The apparatus of claim 1, wherein the first bonding horn is an ultrasonic horn ultrasonic horn positioned adjacently to the anvil.

6. The apparatus of claim 1, wherein the anvil of the second bonding apparatus, in being configured to bond the leg elastic portion of the first web layer and the leg elastic portion of the second web layer absent adhesive, comprises an arrangement of discrete projections that extend outward from a face of the anvil of the second bonding apparatus and form lamination pairs of the plurality of leg bonds, each lamination pair spaced apart greater than a diameter of any of the plurality of leg elastics in an un-tensioned state.

7. The apparatus of claim 1, wherein the anvil of the first bonding apparatus, in being configured to bond the cuff elastic portion to the cuff foldover portion absent adhesive, comprises an arrangement of discrete projections that extend outward from a face of the anvil of the first bonding apparatus and form lamination pairs of the plurality of cuff bonds, each lamination pair spaced apart greater than a diameter of any of the plurality of cuff elastics in an un-tensioned state.

* * * * *